US 8,383,131 B2
Feb. 26, 2013

United States Patent
Roof et al.

(54) PORCINE REPRODUCTIVE AND RESPIRATORY SYNDROME ISOLATES AND METHODS OF USE

(75) Inventors: Michael Roof, Ames, IA (US); Eric Vaughn, Ames, IA (US); Wesley Johnson, Ames, IA (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 0 days.

(21) Appl. No.: 13/085,692

(22) Filed: Apr. 13, 2011

(65) Prior Publication Data

US 2011/0195088 A1 Aug. 11, 2011

Related U.S. Application Data

(63) Continuation of application No. 12/548,597, filed on Aug. 27, 2009, now abandoned, and a continuation of application No. 11/022,262, filed on Dec. 23, 2004, now Pat. No. 7,632,636.

(60) Provisional application No. 60/611,824, filed on Sep. 21, 2004.

(51) Int. Cl.
A61K 39/00 (2006.01)
C12N 7/00 (2006.01)

(52) U.S. Cl. .................... 424/204.1; 435/235.1

(58) Field of Classification Search .............. None
See application file for complete search history.

(56) References Cited

U.S. PATENT DOCUMENTS

| | | |
|---|---|---|
| 3,137,631 A | 6/1964 | Soloway |
| 3,959,457 A | 5/1976 | Speaker et al. |
| 4,015,100 A | 3/1977 | Gnanamuthu et al. |
| 4,122,167 A | 10/1978 | Buynak et al. |
| 4,205,060 A | 5/1980 | Monsimer et al. |
| 4,224,412 A | 9/1980 | Dorofeev et al. |
| 4,452,747 A | 6/1984 | Gersonde et al. |
| 4,468,346 A | 8/1984 | Paul et al. |
| 4,554,159 A | 11/1985 | Roizman et al. |
| 4,606,940 A | 8/1986 | Frank et al. |
| 4,636,485 A | 1/1987 | van der Smissen |
| 4,744,933 A | 5/1988 | Rha et al. |
| 4,753,884 A | 6/1988 | Kit et al. |
| 4,810,493 A | 3/1989 | Patrick et al. |
| 4,921,706 A | 5/1990 | Roberts et al. |
| 4,927,637 A | 5/1990 | Morano et al. |
| 4,944,948 A | 7/1990 | Uster et al. |
| 5,008,050 A | 4/1991 | Cullis et al. |
| 5,009,956 A | 4/1991 | Baumann |
| 5,132,117 A | 7/1992 | Speaker et al. |
| 5,206,163 A | 4/1993 | Renard et al. |
| 5,213,759 A | 5/1993 | Castberg et al. |
| 5,419,907 A | 5/1995 | Paul et al. |
| 5,476,778 A | 12/1995 | Chladek et al. |
| 5,510,258 A | 4/1996 | Sanderson et al. |
| 5,587,164 A | 12/1996 | Sanderson et al. |
| 5,597,721 A | 1/1997 | Brun et al. |
| 5,620,691 A | 4/1997 | Wensvoort et al. |
| 5,674,500 A | 10/1997 | Peeters et al. |
| 5,677,429 A | 10/1997 | Benfield |
| 5,683,865 A | 11/1997 | Collins et al. |
| 5,690,940 A | 11/1997 | Joo |
| 5,695,766 A | 12/1997 | Paul et al. |
| 5,698,203 A | 12/1997 | Visser et al. |
| 5,789,388 A | 8/1998 | Visser et al. |
| 5,840,563 A | 11/1998 | Chladek et al. |
| 5,846,805 A | 12/1998 | Collins et al. |
| 5,858,729 A | 1/1999 | Van Woensel et al. |
| 5,866,401 A | 2/1999 | Hesse |
| 5,888,513 A | 3/1999 | Plana Duran et al. |
| 5,910,310 A | 6/1999 | Heinen et al. |
| 5,925,359 A | 7/1999 | Van Woensel et al. |
| 5,968,525 A | 10/1999 | Fitzgerald et al. |
| 5,976,537 A * | 11/1999 | Mengeling et al. ........ 424/184.1 |
| 5,989,563 A | 11/1999 | Chladek et al. |
| 5,998,601 A | 12/1999 | Murtaugh et al. |
| 6,001,370 A | 12/1999 | Burch et al. |
| 6,015,663 A | 1/2000 | Wesley et al. |
| 6,042,830 A | 3/2000 | Chladek et al. |
| 6,080,570 A | 6/2000 | Chladek et al. |
| 6,110,467 A | 8/2000 | Paul et al. |
| 6,110,468 A | 8/2000 | Collins et al. |
| 6,197,310 B1 | 3/2001 | Wensvoort et al. |
| 6,241,990 B1 | 6/2001 | Collins et al. |
| 6,251,397 B1 | 6/2001 | Paul et al. |
| 6,251,404 B1 | 6/2001 | Paul et al. |
| 6,268,199 B1 | 7/2001 | Meulenberg et al. |
| 6,380,376 B1 | 4/2002 | Paul et al. |
| 6,391,314 B1 | 5/2002 | Allan et al. |

(Continued)

FOREIGN PATENT DOCUMENTS

| | | |
|---|---|---|
| CA | 2103460 A1 | 12/1992 |
| DE | 145705 A1 | 1/1981 |

(Continued)

OTHER PUBLICATIONS

Opriessnig et al (Clinical and Vaccine Immunology 14:1572-1577, 2007).*

(Continued)

Primary Examiner — Mary E Mosher

(74) Attorney, Agent, or Firm — Michael P. Morris; Joyce L. Morrison

(57) ABSTRACT

A method of predicting the virulence of a new or uncharacterized PRRS virus strain is provided wherein the strain is injected into swine and allowed to replicate for a period of from about 3-15 days. During this period, the rate of virus growth and/or the magnitude of viremia is determined, and this data is compared with a corresponding growth rate and/or viremia magnitude of a PRRS virus strain of known virulence, as a measure of the virulence of the new or uncharacterized strain.

4 Claims, 9 Drawing Sheets

U.S. PATENT DOCUMENTS

| | | | |
|---|---|---|---|
| 6,455,245 | B1 | 9/2002 | Wensvoort et al. |
| 6,495,138 | B1 | 12/2002 | van Nieuwstadt et al. |
| 6,498,008 | B2 | 12/2002 | Collins et al. |
| 6,500,662 | B1 | 12/2002 | Calvert et al. |
| 6,592,873 | B1 | 7/2003 | Paul et al. |
| 6,641,819 | B2 | 11/2003 | Mengeling et al. |
| 6,660,513 | B2 | 12/2003 | Mengeling et al. |
| 6,773,908 | B1 | 8/2004 | Paul et al. |
| 6,806,086 | B2 | 10/2004 | Wensvoort et al. |
| 6,841,364 | B2 | 1/2005 | Yuan et al. |
| 6,855,315 | B2 | 2/2005 | Collins et al. |
| 6,982,160 | B2 | 1/2006 | Collins et al. |
| 7,018,638 | B2 | 3/2006 | Chu et al. |
| 7,081,342 | B2 | 7/2006 | Mengeling et al. |
| 7,109,025 | B1 | 9/2006 | Eloit et al. |
| 7,122,347 | B2 | 10/2006 | Verheije et al. |
| 7,132,106 | B2 | 11/2006 | Calvert et al. |
| 7,169,394 | B2 | 1/2007 | Chu et al. |
| 7,211,379 | B2 | 5/2007 | Ellis et al. |
| 7,232,680 | B2 | 6/2007 | Calvert et al. |
| 7,264,804 | B2 | 9/2007 | Collins et al. |
| 7,273,617 | B2 | 9/2007 | Yuan et al. |
| 7,312,030 | B2 | 12/2007 | van Rijn et al. |
| 7,335,361 | B2 | 2/2008 | Liao et al. |
| 7,335,473 | B2 | 2/2008 | Wensvoort et al. |
| 7,368,117 | B2 | 5/2008 | Fetzer et al. |
| 7,618,797 | B2 | 11/2009 | Calvert et al. |
| 7,632,636 | B2 | 12/2009 | Roof et al. |
| 7,691,389 | B2 | 4/2010 | Calvert et al. |
| 7,722,878 | B2 | 5/2010 | Vaughn et al. |
| 7,897,343 | B2 | 3/2011 | Wensvoort et al. |
| 2002/0012670 | A1 | 1/2002 | Elbers et al. |
| 2002/0098573 | A1 | 7/2002 | Meulenberg et al. |
| 2002/0172690 | A1 | 11/2002 | Calvert et al. |
| 2003/0049274 | A1 | 3/2003 | Meulenberg et al. |
| 2003/0118608 | A1 | 6/2003 | Wensvoort et al. |
| 2003/0157689 | A1 | 8/2003 | Calvert et al. |
| 2003/0219732 | A1 | 11/2003 | van Rijn et al. |
| 2004/0009190 | A1 | 1/2004 | Elbers et al. |
| 2004/0132014 | A1 | 7/2004 | Wensvoort et al. |
| 2004/0197872 | A1 | 10/2004 | Meulenberg et al. |
| 2004/0213805 | A1 | 10/2004 | Verheije |
| 2004/0224327 | A1 | 11/2004 | Meulenberg et al. |
| 2004/0253270 | A1 | 12/2004 | Meng et al. |
| 2006/0063151 | A1 | 3/2006 | Roof et al. |
| 2006/0205033 | A1 | 9/2006 | Meulenberg et al. |
| 2006/0240041 | A1 | 10/2006 | Meulenberg et al. |
| 2006/0286123 | A1 | 12/2006 | Fetzer et al. |
| 2007/0003570 | A1 | 1/2007 | Murtaugh et al. |
| 2007/0042000 | A1 | 2/2007 | Mengeling et al. |
| 2009/0148474 | A1 | 6/2009 | Roof et al. |
| 2010/0003278 | A1 | 1/2010 | Roof et al. |
| 2010/0028860 | A1 | 2/2010 | Roof et al. |
| 2010/0129398 | A1 | 5/2010 | Klinge et al. |
| 2011/0104201 | A1 | 5/2011 | Mengeling et al. |
| 2011/0117129 | A1 | 5/2011 | Roof et al. |
| 2011/0195088 | A1 | 8/2011 | Roof et al. |

FOREIGN PATENT DOCUMENTS

| | | | |
|---|---|---|---|
| EP | 208672 | A1 | 1/1987 |
| EP | 0440219 | A1 | 8/1991 |
| EP | 0529584 | A2 | 3/1993 |
| EP | 587780 | A1 | 3/1994 |
| EP | 0595436 | A2 | 5/1994 |
| EP | 0610250 | A1 | 8/1994 |
| EP | 676467 | A2 | 10/1995 |
| EP | 732340 | A2 | 9/1996 |
| EP | 0835929 | A1 | 4/1998 |
| EP | 0835930 | A1 | 4/1998 |
| EP | 0839912 | A1 | 5/1998 |
| EP | 1018557 | A2 | 7/2000 |
| FR | 2602791 | A1 | 2/1988 |
| GB | 2282811 | A | 4/1995 |
| GB | 2289279 | A | 11/1995 |
| JP | 62/198626 | A | 9/1987 |
| WO | 8803410 | A1 | 5/1988 |
| WO | 8908701 | A1 | 9/1989 |
| WO | 9221375 | A1 | 12/1992 |
| WO | 9303760 | A1 | 3/1993 |
| WO | 9306211 | A1 | 4/1993 |
| WO | 9307898 | A1 | 4/1993 |
| WO | 9314196 | A1 | 7/1993 |
| WO | 9418311 | A1 | 8/1994 |
| WO | 9528227 | A1 | 10/1995 |
| WO | 9531550 | A1 | 11/1995 |
| WO | 9604010 | A1 | 2/1996 |
| WO | 9606619 | A1 | 3/1996 |
| WO | 9636356 | A1 | 11/1996 |
| WO | 9640932 | A1 | 12/1996 |
| WO | 9700696 | A1 | 1/1997 |
| WO | 9731651 | A1 | 9/1997 |
| WO | 9731652 | A1 | 9/1997 |
| WO | 9818933 | A1 | 5/1998 |
| WO | 9835023 | A1 | 8/1998 |
| WO | 9850426 | A1 | 11/1998 |
| WO | 9855625 | A1 | 12/1998 |
| WO | 9855626 | A2 | 12/1998 |
| WO | 0053787 | A1 | 9/2000 |
| WO | 0065032 | A1 | 11/2000 |
| WO | 0159077 | A1 | 8/2001 |
| WO | 0190363 | A1 | 11/2001 |
| WO | WO 02/095040 | * | 11/2002 |
| WO | 03062407 | A1 | 7/2003 |
| WO | 2006002193 | A2 | 1/2006 |
| WO | 2006034319 | A2 | 3/2006 |
| WO | 2006074986 | A2 | 7/2006 |
| WO | 2007064742 | A2 | 6/2007 |
| WO | 2008109237 | A2 | 9/2008 |
| WO | 2008121958 | A1 | 10/2008 |
| WO | 2010025109 | A1 | 3/2010 |
| WO | 20110128415 | A1 | 10/2011 |

OTHER PUBLICATIONS

Mengeling et al (American Journal of Veterinary Research 59:1540-1544, 1998).*

Wesley et al, Journal of Veterinary Diagnostic Investigation 10:140-144, 1998.*

Van der Linden et al (Vaccine 21:1952-1957, 2003).*

Verheije et al (Vaccine 21:2556-2563, 2003).*

Thomson et al., "Ontario. Proliferative and necrotizing pneumonia (PNP) of swine: the Ontario situation". Canadian Veterinary Journal, vol. 32, May 1991, p. 313.

Thouless et al., "Isolation of two lapine rotaviruses: Characterization of their subgroup, serotype and RNA electropherotypes". Archives of Virology, vol. 89, Nos. 1-4, 1986, pp. 161-170.

Tian et al., "Emergence of Fatal PRRSV Variants: Unparalleled Outbreaks of Atypical PRRS in China and Molecular Dissection of the Unique Hallmark". PLoS One, vol. 2, No. 6, e526, 2007, pp. 1-10.

Timony, P.J. "Equine Viral Arteritis", Manual of Standards for Diagnostic Tests and Vaccines, 1992, pp. 493-500.

Tobita et al., "Plaque Assay and Primary Isolation of influenza A Viruses in an Established Line of Canine Kidney Cells (MDCK) in the Presence of Trypsin". Medical Microbiology and Immunology, vol. 162, No. 1, Dec. 1975, pp. 9-14.

Todd et al., "Development of an adjuvant-active nonionic block copolymer for use in oil-free subunit vaccines formulations". Vaccine, vol. 15, No. 5, 1997, pp. 564-570.

Travassos et al., "Carajas and Maraba Viruses, Two New Vesiculoviruses Isolated from Phlebotomine Sand Flies in Brazil". American Journal of Tropical Medicine and Hygiene, vol. 33, No. 5, Sep. 1984, pp. 999-1006.

Tsunemitsu et al., "Isolation, characterization, and serial propagation of a bovine group C rotavirus in a monkey kidney cell line (MA104)". Journal of Clinical Microbiology, vol. 29, No. 11, Nov. 1991, pp. 2609-2613.

Ulmer et al., "Enhancement of DNA vaccine potency using conventional aluminum adjuvants". Vaccine, vol. 18, 2000, pp. 18-28.

Urasawa et al., "Sequential Passages of Human Rotavirus in MA-104 Cells". Microbiology and Immunology, vol. 25, No. 10, 1981, pp. 1025-1035.

Van Alstine, W.G., "Mystery Swine Disease in the United States". The New Pig Disease: Porcine Respiration and Reproductive Syndrome. A Report on the Seminar/Workshop Held in Brussels by the European Commission (Directorate-General for Agriculture), Apr. 29-30, 1991, pp. 65-70.

Van Alstine, W.G., "Past Diagnostic Approaches and Findings and Potentially Useful Diagnostic Strategies". Proceedings Mystery Swine Disease Committee Meeting, Oct. 6, 1990, pp. 52-58.

Van Berlo et al., "Equine Arteritis Virus-Infected Cells Contain Six Polyadenylated Virus-Specific RNAs". Virology, vol. 118, 1982, pp. 345-352.

Van Der Linden et al., "Virological kinetics and immunological responses to a porcine reproductive and respiratory syndrome virus infection of pigs at different ages". Vaccine, vol. 21, 2003, pp. 1952-1957.

Van Der Meer et al., "ORF1a-Encoded Replicase Subunits Are Involved in the Membrane Association of the Arterivirus Replication Complex". Journal of Virology, vol. 72, No. 8, 1998, pp. 6689-6698.

Van Der Most et al., "A Domain at the 3' End of the Polymerase Gene Is Essential for Encapsidation of Coronavirus Defective Interfering RNAs". Journal of Virology, vol. 65, No. 6, Jun. 1991, pp. 3219-3226.

Van Dinten et al., "An infectious arterivirus cDNA clone: Identification of a replicase point mutation that abolished discontinuous mRNA transcription". Proceedings of the National Academy of Sciences, vol. 94, Feb. 1997, pp. 997-996.

Van Dinten et al., "Processing of the Equine Arteritis Virus Replicase ORF1b Protein: Identification of Cleavage Products Containing the Putative Viral Polymerase and Helicase Domains". Journal of Virology, vol. 70, No. 10, Oct. 1996, pp. 6625-6633.

Van Dinten et al., "Proteolytic Processing of the Open Reading Frame 1b-Encoded Part of Arterivirus Replicase Is Mediated by nsp4 Serine Protease and Is Essential for Virus Replication". Journal of Virology, vol. 73, No. 3, Mar. 1999, pp. 2027-2037.

Van Marle et al., "Arterivirus discontinuous mRNA transcription is guided by base pairing between sense and antisense transcription-regulating sequences". Proceedings of the National Academy of Sciences, vol. 96, 1999, pp. 12056-12061.

Van Marle et al., "Characterization of an Equine Arteritis Virus Replicase Mutant Defective in Subgenomic mRNA Synthesis". Journal of Virology, vol. 73, No. 7, Jul. 1999, pp. 5274-5281.

Van Marle et al., "Regulation of Coronavirus mRNA Transcription". Journal of Virology, vol. 69, No. 12, Dec. 1995, pp. 7851-7856.

Van Nieuwstadt et al., "Infection with porcine respiratory coronavirus does not fully protect pigs against intestinal transmissable gastroenteritis virus". The Veterinary Record, vol. 125, No. 3, 1989, pp. 58-60.

Van Nieuwstadt et al., "Proteins Encoded by Open Reading Frames 3 and 4 of the Genome of Lelystad Virus (Arteriviridae) Are Structural Proteins of the Virion". Journal of Virology, vol. 70, No. 7, Jul. 1996, pp. 4767-4772.

Van Nieuwstadt et al., "Use of two enzyme-linked immunosorbent assays to monitor antibody responses in swine with experimentally induced infection with porcine epidemic diarrhea virus". American Journal of Veterinary Research, vol. 42, Jul. 1991, pp. 1044-1050.

Van Zijl et al., "Live Attenuated Pseudorabies Virus Expressing Envelope Glycoprotein E1 of Hog Cholera Virus Protects Swine Against Both Pseudorabies and Hog Cholera". Journal of Virology, vol. 65, No. 5, May 1991, pp. 2761-2765.

Vennema et al., "Nucleocapsid-independent assembly of coronavirus-like particles by co-expression of viral envelope protein genes". The EMBO Journal, vol. 15, No. 8, 1996, pp. 2020-2028.

Verheije et al., "Kissing Interaction between 3' Noncoding and Coding Sequences Is Essential for Porcine Arterivirus RNA Replication". Journal of Virology, vol. 76, No. 3, Feb. 2002, pp. 1521-1526.

Verheije et al., "Safety and protective efficacy of porcine reproductive and respiratory syndrome recombinant virus vaccines in young pigs". Vaccine, vol. 21, 2003, pp. 2556-2563.

Veterinary Bulletin, vol. 58, No. 11, 1988, Nos. 6903-6909, p. 932.

Veterinary Bulletin, vol. 60, No. 3, 1990, Nos. 1536-1551, pp. 255-256.

Vieira et al., "New pUC-derived cloning vectors with different selectable markers and DNA replication origins". Gene, vol. 100, 1991, pp. 189-194.

VIIth International Symposium on Nidoviruses (Corona and Arteriviruses), May 20-25, 2000, 32 pages.

Visser, Nicolaas, "Declaration of Dr. N. Visser". Nov. 14, 1995, pp. 1-11.

Von Busse, F.W., Epidemiologic Studies on Porcine Reproductive and Respiratory Syndrome (PRRS). Tierarztliche Umschau, Dec. 1991, pp. 708-717 (Abstract in English p. 711).

Von Ohlinger et al., "Der Seuchenhafte Spatabort beim Schwein Ein Beitrag zur Atiologie des Porcine Reproductive and Respiratory Syndrome (PRRS)". Tierarztl, vol. 46, 1991, pp. 703-708.

Waltner-Toews et al., "A Field Trial to Evaluate the Efficacy of a Combined Rotavirus-Coronavirus/ Escherichia coli vaccine in Dairy Cattle"., Canadian Journal of Comparative Medicine, vol. 49, No. 1, 1985, pp. 1-9.

Wang et al., "Attenuation of porcine reproductive and respiratory syndrome virus strain MN184 using chimeric construction with vaccine sequence". Virology, vol. 371, 2008, pp. 418-429.

Ward et al., "Efficiency of human rotavirus propagation in cell culture". Journal of Clinical Microbiology, vol. 19, No. 6, Jun. 1984, pp. 748-753.

Wardley et al., "The Host Response to African Swine Fever Virus". Progress of Medical Virology, vol. 34, 1987, pp. 180-192.

Wassenaar et al., "Alternative Proteolytic Processing of the Arterivirus Replicase ORF1a Polyprotein: Evidence that NSP2 Acts as a Cofactor for the NSP4 Serine Protease". Journal of Virology, vol. 71, No. 12, Dec. 1997, pp. 9313-9322.

Webster et al., "Chemotherapy and Vaccination: a Possible Strategy for the Control of Highly Virulent Influenza Virus". Journal of Virology, vol. 55, No. 1, 1985, pp. 173-176.

Welch et al., "Construction and evaluation of genetically engineered replication-defective porcine reproductive and respiratory syndrome virus vaccine candidates". Veterinary Immunology and Immunopathology, vol. 102, 2004, pp. 277-290.

Wensvoort et al., "'Blue ear' disease in pigs". Veterinary Record, vol. 128, No. 24, Jun. 1991, p. 574.

Wensvoort et al., "'Lelystad agent'—the cause of abortus blauw (mystery swine disease)". Tijdschr Diergeneeskd, vol. 116, No. 13, Jul. 1991, pp. 675-676.

Wensvoort et al., "An Enzyme Immunoassay Employing Monoclonal Antibodies and Detecting Specifically Antibodies to Classical Swine Fever Virus". Veterinary Microbiology, vol. 17, 1988, pp. 129-140.

Wensvoort et al., "Antigenic Comparison of Lelystad Virus and Swine Infertility and Respiratory Syndrome (SIRS) Virus". Journal of Veterinary Diagnostic Investigation, vol. 4, 1992, pp. 134-138.

Wensvoort et al., "Bovine viral diarrhoea virus infections in piglets born to sows vaccinated against swine fever with contaminated vaccine". Research in Veterinary Science, vol. 45, 1988, pp. 143-148.

Wensvoort et al., "Characterization of Porcine and Some Ruminant Pestiviruses by Cross-neutralization" vol. 20, 1989, pp. 291-306.

Wensvoort et al., "Lelystad virus, the cause of porcine epidemic abortion and respiratory syndrome: a review of mystery swine disease research in Lelystad". Veterinary Microbiology, vol. 33, Nos. 1-4, Nov. 1992, pp. 185-193.

Haynes et al., "Temporal and Morphologic Characterization of the Distribution of Porcine Reproductive and Respiratory Syndrome Virus (PRRSV) by in Situ Hybridization in Pigs Infected with Isolates of PRRSV that Differ in Virulence". Veterinary Pathology, vol. 34, 1997, pp. 39-43.

Heath, et al., "The Behaviour of Some Influenza Viruses in Tissue Cultures of Kidney Cells of Various Species". Archie. f. Virusforschung Bd. VIII, HS, 1958, pp. 577-591.

Hedger et al., "Swine Vesicular Disease Virus". Virus Infections of Porcines, Elsevier Science Publishers, B.V., 1989, pp. 241-250.

Hennen, J., "Statistical methods for longitudinal research on bipolar disorders". Bipolar Disorders, vol. 5, 2003, pp. 156-168.

Hill, Howard, "Overview and History of Mystery Swine". Proceedings of the Mystery Swine Disease Committee Meeting, Denver, CO, Oct. 6, 1990, pp. 29-40.

Hirsch et al., "Ultrastructure of Human Leukocytes After Simultaneous Fixation with Glutaraldehyde and Osmium Tetroxide and "Postfixation" in Uranyl Acetate". The Journal of Cell Biology, vol. 38, 1968, pp. 615-627.

Hofmann et al., "Propagation of the virus of porcine epidemic diarrhea in cell culture". Journal of Clinical Microbiology, vol. 26, No. 11, Nov. 1988, pp. 2235-2239.

Hofmann et al., "Quantitation, biological and physicochemical properties of cell culture-adapted porcine epidemic diarrhea coronavirus (PEDV)". Veterinary Microbiology, vol. 20, No. 2, Jun. 1989, pp. 131-142.

Honda et al., "A Serological Comparison of 4 Japanese Isolates of Porcine Enteroviruses with the International Reference Strains". The Japanese Journal of Veterinary Science, vol. 52, No. 1, 1990, pp. 49-54.

Horowitz et al., "Anti-schistosome monoclonal antibodies of different isotypes—correlation with cytotoxicity". The EMBO Journal, vol. 2, No. 2, 1983, pp. 193-198.

Horsfall et al., "General Principles of Animal Virus Multiplication". Viral and Rickettsial Infections of Man, Fourth Edition, J.B. Lippincott Company, Philadelphia, 1965, pp. 239-241.

Horzinek et al., "Studies on the Substructure of Togaviruses: II. Analysis of Equine Arteritis Rubella, Bovine Viral Diarrhea, and Hog Cholera Viruses". Archiv Für die gesamte Virusforschung, vol. 33, 1971, pp. 306-318.

Hoshino et al., "Isolation and characterization of an equine rotavirus". Journal of Clinical Microbiology, vol. 18, No. 3, Sep. 1983, pp. 585-591.

Hoshino et al., "Serotypic Similarity and Diversity of Rotaviruses of Mammalian and Avian Origin as Studied by Plaque-Reduction Neutralization". The Journal of Infectious Diseases, vol. 149, No. 5, May 1984, pp. 694-702.

Hsue et al., "Characterization of an Essential RNA Secondary Structure in the 3' Untranslated Region of the Murine Coronavirus Genome". Journal of Virology, vol. 74, No. 15, Aug. 2000, pp. 6911-6921.

Huang et al., "Polypyrimidine Tract-Binding Protein Binds to the Complementary Strand of the Mouse Hepatitis Virus 39 Untranslated Region, Thereby Altering RNA Conformation". Journal of Virology, vol. 73, No. 11, Nov. 1999, pp. 9110-9116.

Hurrelbrink et al., "Attenuation of Murray Valley Encephalitis Virus by Site-Directed Mutagenesis of the Hinge and Putative Receptor-Binding Regions of the Envelope Protein". Journal of Virology, vol. 75, No. 16, Aug. 2001, pp. 7692-7702.

Hwang et al., "A 68-Nucleotide Sequence within the 39 Noncoding Region of Simian Hemorrhagic Fever Virus Negative-Strand RNA Binds to Four MA104 Cell Proteins". Journal of Virology, vol. 72, No. 5, May 1998, pp. 4341-4351.

Hyllseth, B., "Structural Proteins of Equine Arteritis Virus". Archiv Für die gesamte Virusforschung, vol. 30, 1973, pp. 177-188.

Iltis et al., "Persistent Varicella-Zoster virus infection in a human rhabdomyosarcoma cell line and recovery of a plaque variant". Infection and Immunity, vol. 37, No. 1, Jul. 1982, pp. 350-358.

Imagawa et al., "Isolation of Foal Rotavirus in MA-104 Cells". Bulleting of Equine Research Institute, vol. 18, 1981, pp. 119-128.

International Search Report and Written Opinion for PCT/US2005/33760 mailed on Apr. 5, 2006.

Izeta et al., "Replication and Packaging of Transmissible Gastroenteritis Coronavirus-Derived Synthetic Minigenomes". Journal of Virology, vol. 73, No. 2, Feb. 1999, pp. 1535-1545.

Jackwood et al., "Replication of Infectious Bursal Disease Virus in Continuous Cell Lines". Avian Diseases, vol. 31, No. 2, Apr.-Jun. 1987, pp. 370-375.

Johnson et al., "Feline panleucopaenia virus. IV. Methods for obtaining reproducible in vitro results". Research in Veterinary Science, vol. 8, No. 2, Apr. 1967, pp. 256-264.

Johnson et al., "Pathogenic and humoral immune responses to porcine reproductive and respiratory syndrome virus (PRRSV) are related to viral load in acute infection". Veterinary Immunology and Immunopathology, vol. 102, No. 3, PRRS Immunology and Immunopathology Special Issue, Dec. 2004, pp. 233-247.

Johnston et al., "Genetic to genomic vaccination". Vaccine, vol. 15, No. 8, 1997, pp. 808-809.

Joo et al., "Encephalomyocarditis Virus As a Potential Cause for Mystery Swine Disease", Livestock Conservation Institute, Proceedings of the Mystery Swine Disease Committee Meeting, Denver, CO, Oct. 6, 1990, pp. 62-66.

Jun et al., "Comparison of Dynamics in Viremia Levels in Chickens Inoculated with Marek's Disease Virus Strains of Different Pathotypes". Virologica Sinica, vol. 16, No. 1, Mar. 2001, pp. 59-63.

Jusa et al., "Effect of heparin on infection of cells by porcine reproductive and respiratory syndrome virus". American Journal of Veterinary Research, vol. 58, No. 5, May 1997, pp. 488-491.

Just et al., "A/New Jersey/76 influenza vaccine trial in seronegative schoolchildren: Comparison of a subunit vaccine with a whole-virus vaccine". Medical Microbiology and Immunology, vol. 164, No. 4, 1978, pp. 277-284.

Kang et al., "Primary Isolation and Identification of Avian Rotaviruses from Turkeys Exhibiting Signs of Clinical Enteritis in a Continuous MA-104 Cell Line". Avian Diseases, vol. 30, 1986, pp. 494-499.

Kapur et al., "Genetic variation in porcine reproductive and respiratory syndrome virus isolates in the midwestern United States". Journal of General Virology, vol. 77, 1996, pp. 1271-1276.

Kasza et al., "Establishment, viral susceptibility and biological characteristics of a swine kidney cell line SK-6". Research in Veterinary Science, vol. 13, No. 1, Jan. 1972, pp. 46-51.

Kasza et al., "Isolation and Characterization of a Rotavirus from Pits". Veterinary Record, vol. 87, 1970, pp. 681-686.

Katz et al., "Antigenic differences between European and American isolates of porcine reproductive and respiratory syndrome virus (PRRSV) are encoded by the carboxyterminal portion of viral open reading frame 3". Veterinary Microbiology, vol. 44, No. 1, Apr. 1995, pp. 65-76.

Keffaber, K., "Reproductive Failure of Unknown Etiology"., AASP Newsletter, vol. 1, No. 2, Sep.-Oct. 1989, pp. 1, 4-5, 8-10.

Keffaber, K.K., "Swine Reproductive Failure of Unknown Etiology". The George A. Young Swine Conference & Annual Nebraska SPF Swine Conference, Aug. 13-14, 1990, pp. 55-67.

Key et al., "Genetic variation and phylogenetic analyses of the ORF5 gene of acute porcine reproductive and respiratory syndrome virus isolates". Veterinary Microbiology, vol. 83, 2001, pp. 249-263.

Kim et al., "Analysis of cis-Acting Sequences Essential for Coronavirus Defective Interfering RNA Replication". Virology, vol. 197, No. 1, Nov. 1993, pp. 53-63.

Kim et al., "Different Biological Characteristics of Wild-Type Porcine Reproductive and Respiratory Syndrome Viruses and Vaccine Viruses and Identification of the Corresponding Genetic Determinants". Journal of Clinical Microbiology, vol. 46, No. 5, May 2008, pp. 1758-1768.

Kim et al., "Enhanced replication of porcine reproductive and respiratory syndrome (PRRS) virus in a homogeneous subpopulation of MA-104 cell line". Archives of Virology, vol. 133, 1993, pp. 477-483.

Klein et al., "Deletion of the IgH enhancer does not reduce immunoglobulin heavy chain production of a hybridoma IgD class switch variant". The EMBO Journal, vol. 3, No. 11, Nov. 1984, pp. 2473-2476.

Klinge et al, "Age-dependent resistance to Porcine reproductive and respiratory syndrome virus replication in swine". Virology Journal, vol. 6, No. 177, Oct. 2009.

Klinge et al., "PRRSV replication and subsequent immune responses in swine of various ages". Abstract of Poster No. 56, International Porcine Reproductive and Respiratory Syndrome (PRRS) Symposium, PRRS and PRRSV-Related Diseases: Prevention and Control Strategies, Chicago, IL, Nov. 30-Dec. 1, 2007.

Klovins et al., "A Long-range Pseudoknot in Qb RNA is Essential for Replication". Journal of Molecular Biology, vol. 294, 1999, pp. 875-884.

Klump et al., "Complete Nucleotide Sequence of Infectious Coxsackievirus B3 cDNA: Two Initial 5' Uridine Residues Are Regained during Plus-Strand RNA Synthesis". Journal of Virology, vol. 64, No. 4, Apr. 1990, pp. 1573-1583.

Klupp et al., "Sequence and expression of the glycoprotein gH gene of pseudorabies virus". Virology, vol. 182, No. 2, Jun. 1991, pp. 732-741.

Knowles et al., "Classification of porcine enteroviruses by antigenic analysis and cytopathic effects in tissue culture: Description of 3 new serotypes". Archives of Virology, vol. 62, No. 3, 1979, pp. 201-208.

Kolodziej et al., "Epitope tagging and protein surveillance". Methods in Enzymology, vol. 194, 1991, pp. 508-519.

Gao et al., "Genomic characterization of two Chinese isolates of Porcine respiratory and reproductive syndrome virus*". Archives of Virology, vol. 149, 2004, pp. 1341-1351.

Cano et al., "Impact of a modfied-live porcine reproductive and respiratory syndrome virus vaccine intervention on a population of pigs infected with a heterologous isolate". Vaccine, vol. 25, 2007, pp. 4382-4391.

"Dutch Team Isolates Mystery Pig Disease Agent", Animal Pharm, vol. 230, Abstract No. 00278268, Jun. 21, 1991, p. 21.

"For purification of viral RNA from Plasma, Serum, Cell-free body fluids, Cell-Culture supernatants". QIAamp® Viral RNA Mini Kit Handbook, QIAGEN, Jan. 1999, Cat #52906, pp. 1-35.

"Frontiers closing to mystery disease pigs". Animal Pharm., No. 228, May 24, 1991, p. 2.

"Revision of the taxonomy of the Coronavirus, Torovirus, and Arterivirus genera". Archives of Virology, vol. 135, 1994, pp. 227-239.

Abstracts of Papers Presented at the 71st Annual Meeting of the Conference of Research Workers in Animal Disease, Nos. 1-6, Nov. 5-6, 1990, 2 pages.

Aksenova et al., "Cultivation of the rabies virus in the continuous kidney cell line 4647 from the green marmoset". Vopr. Virusol., vol. 30, No. 2, 1985, pp. 180-182. (See AXENOVA for English Abstract).

Albina et al., "Immune responses in pigs infected with porcine reproductive and respiratory syndrome virus (PRRSV)". Veterinary Immunology and Immunopathology, vol. 61, 1998, pp. 49-66.

Allan et al., "Experimental infection of colostrum deprived piglets with porcine circovirus 2 (PCV2) and procine reproductive and respiratory syndrome virus (PRRSV) potentiates PCV2 replication". 2000, Archives of Virology, vol. 145, pp. 2421-2429.

Allende et al., "Mutations in the genome of porcine reproductive and respiratory syndrome virus responsible for the attenuated phenotype". Archives of Virology, vol. 145, No. 6, Jun. 2000, pp. 1149-1161.

Allende et al., "North American and European porcine reproductive and respiratory syndrome viruses differ in non-structural protein coding regions". Journal of General Virology, vol. 80, 1999, pp. 307-315.

Altschul et al., "Basic Local Alignment Search Tool". Journal of Molecular Biology, vol. 215, 1990, pp. 403-410.

Andreyev et al., "Genetic variation and phylogenetic relationships of 22 porcine reproductive and respiratory syndrome virus (PRRSV) field strains based on sequence analysis of open reading frame 5". Archives of Virology, vol. 142, 1997, pp. 993-1001.

Ashworth et al., "Antibody-dependent cell-mediated cytotoxicity (ADCC) in Aujeszky's disease". Archives of Virology, vol. 59, No. 4, 1979, pp. 307-318.

Axenova, T.A. "Propagation of Rabies Vaccine Virus in Continuous Green Monkey Kidney Cells 4647". Vopr. Virusol., vol. 30, No. 2, 1985, p. 182. (English Abstract of AKSENOVA Reference.).

Backstrom et al., "Respiratory Diseases of Swine". Veterinary Clinics of North America: Large Animal Practice, vol. 4, No. 2, Nov. 1982, pp. 259-276.

Barfoed et al., "DNA vaccination of pigs with open reading frame 1-7 of PRRS virus". Vaccine, vol. 22, 2004, pp. 3628-3641.

Baric et al., "Interactions between Coronavirus Nucleocapsid Protein and Viral RNAs: Implications for Viral Transcription". Journal of Virology, vol. 62, No. 11, Nov. 1988, pp. 4280-4287.

Baric et al., "Subgenomic Negative-Strand RNA Function during Mouse Hepatitis Virus Infection". Journal of Virology, vol. 74, No. 9, May 2000, pp. 4039-4046.

Bautista et al., "Comparison of Porcine Alveolar Macrophages and CL 2621 for the Detection of Porcine Reproductive and Respiratory Syndrome (PRRS) Virus and Anti-PRRS Antibody". Journal of Veterinary Diagnostic Investigation, vol. 5, No. 2, Apr. 1993, pp. 163-165.

Bautista et al., "Serologic Survey for Lelystad and VR-2332 Strains of Porcine Respiratory and Reproductive Syndrome (PRRS) Virus in US Swine Herds". Journal of Veterinary Diagnostic Investigation, vol. 5, No. 4, Oct. 1992, pp. 612-614.

Beale, AJ, "Vaccines and antiviral drugs". Principles of bacteriology, virology and immunity, vol. 3, Ch. 86, 1984, pp. 147-161.

Beare et al., "Further Studies in Man of Man of HSw1N1 Influenza Viruses". Journal of Medical Virology, vol. 5, 1980, pp. 33-38.

Beghi et al., "Guillain-Barré Syndrome: Clinicoepidemiologic Features and Effect of Influenza Vaccine". Archives of Neurology, vol. 42, No. 11, 1985, pp. 1053-1057.

Benfield et al., "Characterization of swine infertility and respiratory syndrome (SIRS) virus (isolate ATCC VR-2332)". Journal of Veterinary Diagnostic Investigation, vol. 4, 1992, pp. 127-133.

Benfield et al., "Etiologic Agent of Swine Infertility and Respiratory Syndrome in the United States". 72st Annual Meeting of the Conference of Research Workers in Animal Disease, Chicago, IL, Nov. 11-12, 1991, p. 48, Abstract No. 268.

Benfield et al., "Properties of SIRS Virus Isolate ATCC VR-2332 in the United States and Preliminary Characterization of a Monoclonal Antibody to this Virus". American Association of Swine Practitioners Newsletter, vol. 4, No. 4, Jul./Aug. 1992, pp. 19-21.

Berendt et al., "Evaluation of Commercially Prepared Vaccines for Experimentally Induced Type/A/New Jersey/8/76 Influenza Virus Infections in Mice and Squirrel Monkeys". The Journal of Infectious Diseases, vol. 136, Dec. 1977, pp. S712-S718.

Berendt et al., "Reaction of Squirrel Monkeys to Intratracheal Inoculation with Influenza/A/New Jersey/76 (Swine) Virus". Infection and Immunity, vol. 16, No. 2, May 1977, pp. 476-479.

Bilodeau et al., "'Porcine Reproductive and Respiratory Syndrome' in Quebec". The Veterinary Record, Aug. 3, 1991, p. 102.

Blackburn et al., "Use of human influenza vaccine to protect against blue-eared pig disease". Veterinary Record, vol. 129, No. 1, Jul. 1991, p. 19.

Bohl et al., "Isolation and Serotyping of Porcine Rotaviruses and Antigenic Comparison with Other Rotaviruses". Journal of Clinical Microbiology, vol. 19, No. 2, Feb. 1984, pp. 105-111.

Bouillant et al., "Viral Susceptibility of a Cell Line Derived from the Pig Oviduct". Canadian Journal of Comparative Medicine, vol. 39, 1975, pp. 450-456.

Boursnell et al., "Sequence of the membrane protein gene from avian coronavirus IBV". Virus Research, vol. 1, 1984, pp. 303-313.

Boursnell et all., "Completion of the Sequence of the Genome of the Coronavirus Avian Infectious Bronchitis Virus". Journal of General Virology, vol. 68, 1987, pp. 57-77.

Bowie et al., "Deciphering the Message of Protein Sequences: Tolerance to Amino Acid Substitutions". Science, vol. 247, 1990, pp. 1306-1310.

Boyer et al., "Infectious Transcripts and cDNA Clones of RNA Viruses". Virology, vol. 198, No. 2, Feb. 1994, pp. 415-426.

Bramel-Verheije et al., "Expression of a Foreign Epitope by Porcine Reproductive and Respiratory Syndrome Virus". Virology, vol. 278, 2000, pp. 380-389.

Bredenbeek et al., "The primary structure and expression of the second open reading frame of the polymerase gene of the coronavirus MHV-A59; a highly conserved polymerase is expressed by an efficient ribosomal frameshifting mechanism". Nucleic Acids Research, vol. 18, No. 7, 1990, pp. 1825-1832.

Brenner et al., "A Negative Staining Method for High Resolution Electron Microscopy of Viruses". Biochimica Et Biophysica Acta, vol. 34, 1959, pp. 103-110.

Brinton-Darnell et al., "Structure and chemical-physical characteristics of lactate dehydrogenase-elevating virus and its RNA". Journal of Virology, vol. 16, No. 2, Aug. 1975, pp. 420-433.

Brinton-Darnell, M. "Lactate Dehydrogenase-Elevating, Equine Arteritis and Lelystad Viruses". Encyclopedia of Virology, vol. 2, 1999, pp. 763-771.

Bruner, D.W., "Table XXXII. Characteristics of Viral Respiratory Infections in Swine" Hagan's Infectious Diseases of Domestic Animals: With Special Reference to Etiology, Diagnosis, and Biologic Therapy, Sixth Edition, Comstock Publishing Associations, a division of Cornell University Press, Ithaca and London, 1973, 5 pages.

Brüggemann et al., "Immunoglobulin V region variants in hybridoma cells. I. Isolation of a variant with altered idiotypic and antigen binding specificity". The EMBO Journal, vol. 1, No. 5, 1982, pp. 629-634.

Buck, K. W., "Comparison of the Replication of Positive-Stranded RNA Viruses of Plants and Animals". Advances in Virus Research, vol. 47, 1996, pp. 159-251.

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue". The Journal of Cell Biology, vol. 111, 1990, pp. 2129-2138.

Burroughs, et al., "Relationship of San Miguel Sea Lion Virus to Other Members of the Calicivirus Group". Intervirology, vol. 10, 1978, pp. 51-59.

Cabasso et al., "Propagation of Infectious Canine Hepatitis Virus in Tissue Culture". Proceedings of the Society for Experimental Biology and Medicine, vol. 85, 1954, pp. 239-245.

Caeiro et al., "In vitro DNA replication by cytoplasmic extracts from cells infected with African swine fever virus". Virology, vol. 179, No. 1, Nov. 1990, pp. 87-94.

Callebaut et al., "Antigenic Differentiation between Transmissible Gastroenteritis Virus of Swine and a Related Porcine Respiratory Coronavirus". Journal of General Virology, vol. 69, 1988, pp. 1725-1730.

Carrascosa et al., "Relationship of San Miguel Sea Lion Virus to Other Members of the Calicivirus Group". Journal of Virological Methods, vol. 3, No. 6, Jan. 1982, pp. 303-310.

Drew, T., "Porcine Reproductive and Respiratory Syndrome Virus: A Review". Apr. 1996, 3 pages.

Duan et al., "Identification of a putative Receptor for Porcine Reproductive and Respiratory Syndrome Virus on Porcine Alveolar Macrophages". Journal of Virology, vol. 72, No. 5, May 1998, pp. 4520-4523.

Duran et al. "Recombinant Baculovirus Vaccines Against Porcine Reproductive and Respiratory Syndrome (PRRS)". Abstracts PRRS, Aug. 9th to 10th, 1995, Copenhagen, Denmark, 2 pages.

Dykhuizen et al., "Determining the Economic Impact of the 'New' Pig Disease", Porcine Reproductive and Respiratory Syndrome, A Report on the Seminar Held in Brussels on Nov. 4-5, 1991 and Organized by the European Commission, pp. 53-60.

Easterday, B.C., "Swine Influenza". Diseases of Swine, Sixth Edition, Iowa State University Press, 1986, pp. 244-315. (Part One of Two-pp. 244-285). This NPL is too large for EFS submission. Therefore filing in two parts.

Easterday, B.C., "Swine Influenza". Diseases of Swine, Sixth Edition, Iowa State University Press, 1986, pp. 244-315. (Part Two of Two-pp. 286-315). This NPL is too large for EFS submission. Therefore filing in two parts.

Easterday, et al., "Swine Influenza". In Diseases of Swine (8th Edition), BE Straw, S D'Allaire, WI. Mengeling, DJ Taylor, eds., Ames: Iowa State University Press, 1999, pp. 277-290.

Edwards et al., "Oligodeoxyribonucleotide ligation to single-stranded cDNAs: a new tool for cloning 5' ends of mRNAs and for constructing cDNA libraries by in vitro amplification". Nucleic Acids Research, vol. 19, No. 19, pp. 5227-5232. (1991).

Ehresmann et al., "RNA synthesized in calicivirus-infected cells is atypical of picornaviruses". Journal of Virology, vol. 22, No. 2, May 1977, pp. 572-576.

Ellis, R.W., "New Technologies for Making Vaccines". Vaccines, Chapter 29, Plotkin et al Eds., WB Saunders Company, Philadelphia, PA, 1988, pp. 568-575.

Enjuanes et al., "Isolation and Properties of the DNA of African Swine Fever (ASF) Virus". Journal of General Virology, vol. 32, No. 3, Sep. 1976, pp. 479-492.

*Enzo Biochem Inc.* v. *Gen-Probe Incorporated et al.*, No. 01-01230; Decided Jul. 15, 2002.

Estes et al., "Simian rotavirus SA11 replication in cell cultures". Journal of Virology, vol. 31, No. 3, Sep. 1979, pp. 810-815.

Fang et al., "Heterogeneity in nsp2 of European-like porcine reproductive and respiratory syndrome viruses isolated in the United States". Virus Research, vol. 100, 2004, pp. 229-235.

Fenner et al., "Immunization against Viral Diseases", Veterinary Virology, Ch. 14, 1992, pp. 265-271.

Fenner et al., "Viral Genetics and Evolution", Veterinary Virology, Ch. 5, 1992, pp. 89-95.

Ferrari et al., "Isolation of Cytopathic Strains of Rotavirus from Pigs". Microbiologica, vol. 9, No. 3, Jul. 1986, pp. 287-294.

Flint et al., "Virus Cultivation, Detection, and Genetics". Virology, Molecular Biology, Pathogenesis, and Control, Ch. 2, 2000, pp. 40-42.

Foss et al., "Adjuvant Danger Signals Increase the Immune Response to Porcine Reproductive and Respiratory Syndrome Virus". Viral Immunology, vol. 15, No. 4, 2002, pp. 557-566.

Frolov et al., "Alphavirus-based expression vectors: Strategies and applications". Proceedings of the National Academy of Sciences, vol. 93, Oct. 1996, pp. 11371-11377.

Fu et al., "Detection and survival of group a rotavirus in a piggery". Veterinary Record, vol. 125, 1989, pp. 576-578.

Fukuhara et al., "Evidence for endocytosis-independent infection by human rotavirus". Archives of Virology, vol. 97, Nos. 1-2, 1987, pp. 93-99.

Funkhouser et al., "Mutations in the 5'-noncoding, 2C and P3 Regions of the Genome Increase the Efficiency of Hepatitis A Virus Growth in MRC-5 Cells". Vaccines, vol. 94, Cold Springs Harbor Laboratory Press, 1994, pp. 345-349.

Garwes, D.J., "Transmissible gastroenteritis". Veterinary Record, vol. 122, 1988, pp. 462-463.

Geisbert et al., "Use of Immunoelectron Microscopy to Show Ebola Virus During the 1989 United States Epizootic". Journal of Clinical Pathology, vol. 43, No. 10, Oct. 1990, pp. 813-816.

Girard et al., "Experimentally induced porcine proliferative and necrotising pneumonia with an influenza A virus". The Veterinary Record, vol. 130, Mar. 1992, pp. 206-207.

Godeny et al., "Map location of lactate dehydrogenase-elevating virus (LDV) capsid protein (Vpl) gene", Virology, vol. 177, No. 2, Aug. 1990, pp. 768-771.

Godeny et al., "The 3' Terminus of Lactate Dehydrogenase-Elevating Virus Genome RNA Does Not Contain Togavirus or Flavivirus Conserved Sequences", Virology, vol. 72, 1989, pp. 647-650.

Goldfield et al., "Influenza in New Jersey in 1976: Isolations of Influenza A/New Jersey/76 Virus at Fort Dix". The Journal of Infectious Diseases, vol. 136, Supp. 3, 1977, pp. S347-S355.

Goldstein, et al., "Evaluation of Three Cell Culture Systems as Substrates for Influenza Virus Assay". Applied Microbiology, vol. 19, No. 4, Apr. 1970, pp. 580-582.

Gong et al., "Characterization of RNA synthesis during a one-step growth curve and of the replication mechanism of bovine viral diarrhoea virus". Journal of General Virology, vol. 77, 1996, pp. 2729-2736.

Gorcyca et al., RespPRRS: A new tool for the prevention and control of PRRS in pigs. Proceedings of the American Association of Swine Practitioners, Omaha, Nebraska, Mar. 1995, pp. 1-22.

Gourreau et al., "Diffusion du virus de la grippe du porc (H1N1=Hsw1N1) en France". Annales de l'Institut Pasteur/Virologie, vol. 132, No. 2, Apr.-Jun. 1981, pp. 287-294.

Goyal, S., "Porcine Reproductive and Respiratory Syndrome", Journal of Veterinary Diagnostic Investigation, vol. 5, No. 4, 1993, pp. 656-664.

Gravell et al., "Differences among isolates of simian hemorrhagic fever (SHF) virus". Proceedings of the Society for Experimental Biology and Medicine, vol. 181, No. 1, 1986, pp. 112-119.

Graves, J.H., "Swine Vesicular Disease". Diseases of Swine, Fifth Edition, Chapter 23, The Iowa State University Press, Ames, Iowa, 1958, pp. 288-293.

Grebennikova et al., "Genomic characterization of virulent, attenuated, and revertant passages of a North American porcine reproductive and respiratory syndrome virus strain". Virology, vol. 321, 2004, pp. 383-390.

Greiner et al., "Quantitative relationship of systemic virus concentration on growth and immune response in pigs". Journal of Animal Science, vol. 78, 2000, pp. 2690-2695.

Grizzard et al., "Experimental production of respiratory tract disease in cebus monkeys after intratracheal or intranasal infection with influenza A/Victoria/3/75 or influenza A/New Jersey/76 virus". Infection and Immunity, vol. 21, No. 1, Jul. 1978, pp. 201-205.

Grouse, L.D., "Swine Flue Sequelae"., Journal of the American Medical Association, vol. 243, No. 24, 1980, p. 2489.

Grunert et al., "Sensitivity of Influenza A/New Jersey/8/76 (HswlNl) Virus to Amantadine-HCl". Journal of Infectious Diseases, vol. 136, No. 2, 1977, pp. 297-300.

Guan et al., "Requirement of a 5?-Proximal Linear Sequence on Minus Strands for Plus-Strand Synthesis of a Satellite RNA Associated with Turnip Crinkle Virus". Virology, vol. 268, No. 2, Mar. 2000, pp. 355-363.

Gubler et al., "A simple and very efficient method for generating cDNA libraries". Gene, vol. 25, 1983, pp. 263-269.

Gustafson, D.P., "Pseudorabies". Diseases of Swine, Fifth Edition, Ch. 14, The Iowa State University Press, Ames, Iowa, 1981, pp. 209-223.

Halbur et al., "Comparative pathogenicity of nine US porcine reproductive and respiratory syndrome virus (PRRSV) isolates in a five-week-old cesarean-derived, colostrum-deprived pig model". Journal of Veterinary Diagnostic Investigation, vol. 8, 1996, pp. 11-20.

Halbur et al., "Effects of different US isolates of porcine reproductive and respiratory syndrome virus (PRRSV) on blood and bone marrow parameters of experimentally infected pigs". Veterinary Record, vol. 151, 2002, pp. 344-348.

Halbur et al., "Variable Pathogenicity of Nine Porcine Reproductive and Respiratory Syndrome Virus (PRRSV) Isolates". Conference of Research Workers in Animal Diseases, Abstracts of Papers, Chicago, Illinois, paper #222, Nov. 1993.

Halbur et al., "Viral Pneumonia in Neonatal and Nursery pigs. Experimental Work with SIRS Agent and Evidence of Another New Viral Agent". Agri-Practice, vol. 12, No. 1, Jan.-Feb. 1991, pp. 23-34.

Hao et al., "Polymorphic genetic characterization of the ORF7 gene of porcine reproductive and respiratory syndrome virus (PRRSV) in China". Virology Journal, vol. 8:73, pp. 1-9, (2011).

Harlow & Lane, Editors, "Antibodies, a Laboratory Manual". Cold Spring Harbor: Cold Spring Harbor Laboratory, New York, 1988, pp. 423, 464-468.

Rossow, K.D., "Porcine Reproductive and Respiratory Syndrome". Veterinary Pathology, vol. 35, 1998, pp. 1-20.

Roth et al., "Influenza virus hemagglutinin expression is polarized in cells infected with recombinant SV40 viruses carrying cloned hemagglutinin DNA". Cell, vol. 33, No. 2, Jun. 1983, pp. 435-443.

Roth et al., "The large external domain is sufficient for the correct sorting of secreted or chimeric influenza virus hemagglutinins in polarized monkey kidney cells". The Journal of Cell Biology, vol. 104, Mar. 1987, pp. 769-782.

Rottier et al., "Predicted Membrane Topology of the Coronavirus Protein E1". Biochemistry, vol. 25, 1986, pp. 1335-1339.

Rovira et al., "Experimental Inoculation of Conventional Pigs with Porcine Reproductive and Respiratory Syndrome virus and Porcine Circovirus 2", J. Virol, jApr. 2002, vol. 76, No. 7, pp. 3232-3239.

Sagripanti et al., "The Cap Structure of Simian Hemorrhagic Fever Virion RNA". Virology, vol. 151, 1986, pp. 143-150.

Saif et al., "Serial propagation of porcine group C rotavirus (pararotavirus) in a continuous cell line and characterization of the passaged virus". Journal of Clinical Microbiology, vol. 26, No. 7, Jul. 1988, pp. 1277-1282.

Saif, L.J., "Coronavirus Immunogens". Veterinary Microbiology, vol. 37, No. 3-4, Nov. 1993, pp. 285-297.

Sarnow, P. "Role of 3'-End Sequences in Infectivity of Poliovirus Transcripts Made In Vitro". Journal of Virology, vol. 63, No. 1, Jan. 1989, pp. 467-470.

Sawicki et al., "Coronavirus Transcription: Subgenomic Mouse Hepatitis Virus Replicative Intermediates Function in RNA Synthesis". Journal of Virology, vol. 64, No. 3, Mar. 1990, pp. 1050-1056.

Schmidt et al., "Infection of Influenza A Viruses of Tracheal Organ Cultures Derived from Homologous and Heterologous Hosts". The Journal of Infectious Diseases, vol. 129, No. 1, 1974, pp. 28-36.

Scott, F.W., "Immunization against feline coronaviruses". Advances in Experimental Medicine and Biology, vol. 218, 1987, pp. 569-576.

Seal et al., "Analysis of the Serologic Relationship among San Miguel Sea Lion Virus and Vesicular Exanthema of Swine Virus Isolates. Application of the Western Blot Assay for Detection of Antibodies in Swine Sera to these Virus Types". Journal of Veterinary Diagnostic Investigation, vol. 7, No. 2, Apr. 1995, pp. 190-195.

Seal et al., "Isolation of caliciviruses from skunks that are antigenically and genotypically related to San Miguel sea lion virus Original Research". Virus Research, vol. 37, No. 1, Jun. 1995, pp. 1-12.

Seneca, H., "Influenza: epidemiology, etiology, immunization and management". Journal of American Geriatrics Society, vol. 28, No. 6, Jun. 1980, pp. 241-250.

Sethna et al., "Coronavirus subgenomic minus-strand RNAs and the potential for mRNA replicons". Proceedings of the National Academy of Sciences, vol. 86, Jul. 1989, pp. 5626-5630.

Setzer et al., "Size Heterogeneity in the 3' End of Dihydrofolate Reductase Messenger RNAs in Mouse Cells". Cell, vol. 22, Nov. 1980, pp. 361-370.

Shaw et al., "Experimental rotavirus infection in three-week-old pigs". American Journal of Veterinary Research, vol. 50, No. 11, Nov. 1989, pp. 1961-1965.

Shen et al., "Determination of the complete nucleotide sequence of a vaccine strain of porcine reproductive and respiratory syndrome virus and identification of the Nsp2 gene with a unique insertion". Archives of Virology, vol. 145, No. 5, May 2000, pp. 871-883.

Shibata et al., "Detection of Human Papilloma Virus in Paraffin-Embedded Tissue Using the Polymerase Chain Reaction". The Journal of Experimental Medicine, vol. 167, No. 1, Jan. 1988, pp. 225-230.

Shieh et al., "The 5'-End Sequence of the Murine Coronavirus Genome: Implications of Multiple Fusion Sites in Leader-Primed Transcription". Virology, vol. 156, 1987, pp. 321-330.

Shin et al., "Assessment of Porcine Reproductive and Respiratory Syndrome Virus RNA Load in Sera and Tissues during Acute Infection". Journal of Veterinary Science, vol. 3, No. 2, 2002, pp. 75-85.

Shope et al., "The Susceptibility of Swine to the Virus of Human Influenza". Annual Meeting of the Society of American Bacteriologists in New York, 1936, pp. 791-801.

Shortridge et al., "Geographical Distribution of Swine (HSw1N1) and Hong Kong (H3N2) Influenza Virus Variants in in Pigs in Southeast Asia". Intervirology, vol. 11, No. 1, 1979, pp. 9-15.

Skiadopoulos et al., "Identification of Mutations Contributing to the Temperature-Sensitive, Cold-Adapted, and Attenuation Phenotypes of the Live-Attenuated Cold-Passage 45 (cp45) Human Parainfluenza Virus 3 Candidate Vaccine". Journal of Virology, vol. 73, No. 2, Feb. 1999, pp. 1374-1381.

Smith et al., "Isolation of Swine Influenza Virus from Autopsy Lung Tissue of Man". New England Journal of Medicine, vol. 294, Mar. 1976, pp. 708-710.

Smith et al., "San Miguel Sea Lion Virus Isolation, Preliminary Characterization and Relationship to Vesicular Exanthema of Swine Virus". Nature, vol. 244, Jul. 1973, pp. 108-110.

Snijder et al., "A 3'-Coterminal Nested Set of Independently Transcribed mRNAs Is Generated during Berne Virus Replication". Journal of Virology, vol. 64, No. 1, Jan. 1990, pp. 331-338.

Snijder et al., "Identification of a Novel Structural Protein of Arteriviruses". Journal of Virology, vol. 73, No. 8, Aug. 1999, pp. 6335-6345.

Snijder et al., "Non-structural proteins 2 and 3 interact to modify host cell membranes during the formation of the arterivirus replication complex". Journal of General Virology, vol. 83, 2001, pp. 985-994.

Snijder et al., "Proteolytic Processing of the Replicase ORF1a Protein of Equine Arteritis Virus". Journal of Virology, vol. 68, No. 9, Sep. 1994, pp. 5755-5764.

Snijder et al., "The carboxyl-terminal part of the putative Berne virus polymerase is expressed by ribosomal frameshifting and contains sequence motifs which indicate that toro- and coronaviruses are evolutionarily related". Nucleic Acids Research, vol. 18, No. 15, Aug. 1990, pp. 4535-4542.

Snijder et al., "The molecular biology of arteriviruses". Journal of General Virology, vol. 79, 1998, pp. 961-979.

Snijder et al., "Toroviruses: replication, evolution and comparison with other members of the coronavirus-like superfamily". Journal of General Virology, vol. 74, 1993, pp. 2305-2316.

Spaan et al., "Coronaviruses: Structure and Genome Expression". Journal of General Virology, vol. 69, 1988, pp. 2939-2952.

Stephen et al., "Swine Influenza Virus Vaccine: Potentiation in Rhesus Monkeys in Antibody Responses by a Nuclease Resistant Derivative of Ply I-Poly C". U.S. Army Medical Research Institute of Infectious Diseases, Fort Detrick, Frederick, MD 21701, 1976, 10 pages.

Stephen et al., "Swine influenza virus vaccine: potentiation of antibody responses in rhesus monkeys". Science, vol. 197, No. 4310, 1977, pp. 1289-1290.

Stevenson et al., "Endemic Porcine Reproductive and Respiratory Syndrome Virus Infection of Nursery Pigs in Two Swine Herds without Current Reproductive Failure". Journal of Veterinary Diagnostic Investigation, vol. 5, 1993, pp. 432-434.

Stim, T.B., "Arbovirus Plaquing in Two Simian Kidney Cell Lines". Journal of General Virology, vol. 5, No. 3, Oct. 1969, pp. 329-338.

Suarez et al., "Direct detection of the porcine reproductive and respiratory syndrome (PRRS) virus by reverse polymerase chain reaction (RT-PCR)". Archives of Virology, vol. 135, No. 1-2, 1994, pp. 89-99.

Suarez et al., "Phylogenetic relationships of European strains of porcine reproductive and respiratory syndrome virus (PRRSV) inferred from DNA sequences of putative ORF-5 and ORF-7 genes". Virus Research, vol. 42, Nos. 1-2, Jun. 1996, pp. 159-165.

Sumiyoshi et al., "Infectious Japanese Encephalitis Virus RNA Can Be Synthesized from In Vitro-Ligated cDNA Templates". Journal of Virology, vol. 66, No. 9, Sep. 1992, pp. 5425-5431.

Tahara et al., "Coronavirus Translational Regulation: Leader Affects mRNA Efficiency". Virology, vol. 202, No. 1, Aug. 1994, pp. 621-630.

Tao et al., "Host Range Restriction of Parainfluenza Virus Growth Occurs at the Level of Virus Genome Replication". Virology, vol. 220, 1996, pp. 69-77.

Tauraso et al., "Simian Hemorrhagic Fever: III. Characterization of a Viral Agent". The American Journal of Tropical Medicine and Hygiene, vol. 17, No. 3, May 1968, pp. 422-431.

Terpstra et al., "Experimental reproduction of porcine epidemic abortion and respiratory syndrome (mystery swine disease) by infection with Lelystad virus: Koch's postulates fulfilled". The Veterinary Quarterly, vol. 13, No. 3, Jul. 1991, pp. 131-136.

Thacker, B., "Clinical Manifestations of PRRS Virus". 2003 PRRS Compendium: Second Edition, National Pork Board, Des Moines, IA, 2003, pp. 7-15.

Thanawongnuwech et al., "Effects of Low (Modified-live Virus Vaccine) and High (VR-2385)-Virulence Strains of Porcine Reproductive and Respiratory Syndrome Virus on Pulmonary Clearance of Copper Particles in Pigs". Veterinary Pathology, vol. 35, 1998, pp. 398-406.

Theil et al., "Isolation and Serial Propagation of Turkey Rotaviruses in a Fetal Rhesus Monkey Kidney (MA104) Cell Line". Avian Diseases, vol. 30, No. 1, 1985, pp. 93-104.

Theil et al., "Partial characterization of a bovine group A rotavirus with a short genome electropherotype". Journal of Clinical Microbiology, vol. 26, No. 6, Jun. 1988, p. 1094-1099.

Kouvelos et al., "Comparison of Bovine, Simian and Human Rotavirus Structural Glycoproteins". Journal of General Virology, vol. 65, Jul. 1984, pp. 1211-1214.

Kreutz, L.C., "Cellular membrane factors are the major determinants of porcine reproductive and respiratory syndrome virus tropism". Virus Research, vol. 53, 1998, pp. 121-128.

Kundin, W.D., "Hong Kong A-2 Influenza Virus Infection among Swine during a Human Epidemic in Taiwan". Nature, vol. 228, Nov. 1970, p. 857.

Kuo et al., "A Nested Set of Eight RNAs Is Formed in Macrophages Infected with Lactate Dehydrogenase-Elevating Virus", Journal of Virology, vol. 65, No. 9, Sep. 1991, pp. 5118-5123.

Kusanagi et al., "Isolation and Serial Propagation of Porcine Epidemic Diarrhea Virus in Cell Cultures and Partial Characterization of the Isolate". Journal of Veterinary Medical Science, vol. 54, No. 2, 1992, pp. 313-318.

Kutsuzawa et al., "Isolation of Human Rotavirus Subgroups 1 and 2 in Cell Culture". Journal of Clinical Microbiology, vol. 16, No. 4, Oct. 1982, pp. 727-730.

Kwang et al., "Cloning, expression, and sequence analysis of the ORF4 gene of the porcine reproductive and respiratory syndrome virus MN-1b". Journal of Veterinary Diagnostic Investigation, vol. 6, No. 3, Jul. 1994, pp. 293-296.

Labarque et al., "Effect of cellular changes and onset of humoral immunity on the replication of porcine reproductive and respiratory syndrome virus in the lungs of pigs". Journal of General Virology, vol. 81, 2000, pp. 1327-1334.

Labarque et al., "Respiratory tract protection upon challenge of pigs vaccinated with attenuated porcine reproductive and respiratory syndrome virus vaccines". Veterinary Microbiology, vol. 95, 2003, pp. 187-197.

Lai et al., "Coronavirus: how a large RNA viral genome is replicated and transcribed". Infectious Agents and Disease, vol. 3, Nos. 2-3, 1994, pp. 98-105.

Lai et al., "Coronavirus: organization, replication and expression of genome". Annual Review of Microbiology, vol. 33, 1990, pp. 303-333.

Lai et al., "Infectious RNA transcribed from stably cloned full-length cDNA of dengue type 4 virus". Proceedings of the National Academy of Sciences, vol. 88, Jun. 1991, pp. 5139-5143.

Lazar et al., "Transforming Growth Factor a: Mutation of Aspartic Acid 47 and Leucine 48 Results in Different Biological Activities". Molecular and Cellular Biology, vol. 8, No. 3, Mar. 1988, pp. 1247-1252.

Leitner et al., "DNA and RNA-based vaccines: principles, progress and prospects". Vaccine, vol. 18, 2000, pp. 765-777.

Levy et al., "Freeze-drying is an effective method for preserving infectious type C retroviruses". Journal of Virological Methods, vol. 5, Nos. 3-4, Nov. 1982, pp. 165-171.

Liljestrom et al., "A New Generation of Animal Cell Expression Vectors Based on the Semliki Forest Virus Replicon". Nature Biotechnology, vol. 9, 1991, pp. 1356-1361.

Lin et al., "Deletion Mapping of a Mouse Hepatitis Virus Defective Interfering RNA Reveals the Requirement of an Internal and Discontiguous Sequence fro Replication". Journal of Virology, vol. 67, No. 10, Oct. 1993, pp. 6110-6118.

Lin et al., "Identification of the cis-Acting Signal for Minus-Strand RNA Synthesis of a Murine Coronavirus: Implications for the Role of Minus-Strand RNA in RNA Replication and Transcription". Journal of Virology, vol. 68, No. 12, Dec. 1994, pp. 8131-8140.

Lin et al., "The 3' Untranslated Region of Coronavirus RNA Is Required for Subgenomic mRNA Transcription from a Defective Interfering RNA". Journal of Virology, vol. 70, No. 10, Oct. 1995, pp. 7236-7240.

Liu et al., "A Specific Host Cellular Protein Binding Element Near the 3? End of Mouse Hepatitis Virus Genomic RNA". Virology, vol. 232, No. 1, May 1997, pp. 74-85.

Loula, T., "Clinical Presentation of Mystery Pig Disease in the Breeding Herd and Suckling Piglets". Proceedings of the Mystery Swine Disease Committee Meeting, Denver, CO, Oct. 6, 1990, pp. 37-40.

Loula, T., "Mystery Pig Disease", Agri-Practice, vol. 12, No. 1, Jan.-Feb. 1991, pp. 29-34.

Luytjes et al., "Replication of Synthetic Defective Interfering RNAs Derived from Coronavirus Mouse Hepatitis Virus-A59". Virology, vol. 216, No. 1, Feb. 1996, pp. 174-183.

Lv et al., "An infectious cDNA clone of a highly pathogenic porcine reproductive and respiratory syndrome virus variant associated with porcine high fever syndrome". Journal of General Virology, vol. 89, 2008, pp. 2075-2079.

Madec et al., "Consequences pathologiques d'un episode grippal severe (virus swine A/H1N1 dans les conditions naturelles chez la truie non immune en debut de gestation". Comparative Immunology, Microbiology and Infectious Diseases, vol. 12, Nos. 1-2, 1989, pp. 17-27.

Madin, S.H. "Vesicular Exanthema Virus". Virus Infections of Porcines, Elsevier Science Publishers B.V., 1989, pp. 267-271.

Makabe et al., "Hemagglutination with Ovine Rotavirus". Archives of Virology, vol. 90, 1986, pp. 153-158.

Makino et al., "Leader sequences of murine coronavirus mRNAs can be freely reassorted: Evidence for the role of free leader RNA in transcription". Proceedings of the National Academy of Sciences, vol. 83, Jun. 1986, pp. 4204-4208.

Makino et al., "Primary Structure and Translation of a Defective Interfering RNA of Murine Coronavirus". Virology, vol. 166, 1988, pp. 550-560.

Mardassi et al., "Identification of major differences in the nucleocapsid protein genes of a Québec strain and European strains of porcine reproductive and respiratory syndrome virus". vol. 75, No. 3, Mar. 1994, pp. 681-685.

Mardassi et al., "Molecular analysis of the ORFs 3 to 7 of porcine reproductive and respiratory syndrome virus, Québec reference strain". Archives of Virology, vol. 140, No. 8, 1995, pp. 1405-1418.

Mason, P.W., "Maturation of Japanese encephalitis virus glycoproteins produced by infected mammalian and mosquito cells". Virology, vol. 169, No. 2, Apr. 1989, pp. 354-364.

Masters et al., "Functions of the coronavirus nucleocapsid protein". Coronaviruses and Their Diseases, Plenum Press, New York, pp. 235-238, (1990).

Masurel, N., "Swine Influenza Virus and the Recycling of Influenza-A Viruses in Man". The Lancet, Jul. 31, 1976, pp. 244-247.

McAuliffe et al., "Codon Substitution Mutations at Two Positions in the L Polymerase Protein of Human Parainfluenza Virus Type 1 Yield Viruses with a Spectrum of Attenuation In Vivo and Increased Phenotypic Stability In Vitro". Journal of Virology, vol. 78, No. 4, Feb. 2004, pp. 2029-2036.

McCullough et al., "9. Experimental Transmission of Mystery Swine Disease", The New Pig Disease Porcine Respiration and Reproductive Syndrome, A report on the seminar/workshop held in Brussels on Apr. 29-30, 1991, pp. 46-52.

McDaniel, H.A., "African Swine Fever". Diseases of Swine, 5th Edition, Chapter 18, The Iowa State University Press, Ames, Iowa, 1981, pp. 237-245.

McFerran, J.B., "Reovirus Infection". Diseases of Swine, Fifth Edition, Chapter 28, The Iowa State University Press, Ames, Iowa, 1981, pp. 330-334.

McIntosh, "Diagnostic Virology". Fields Virology, Ch. 17, Second Edition, vol. 1, 1990, pp. 411-437.

McKinney, W.P., "Fatal Swine Influenza Pneumonia During Late Pregnancy". Archives of Internal Medicine, vol. 150, No. 1, Jan. 1990, pp. 213-215.

McQueen et al., "Influenza in animals". Advances in Veterinary Science, vol. 12, 1968, pp. 285-336.

Meikeljohn et al., "Respiratory Virus Vaccine Evaluation and Surveillance". Semi-Annual Contract Progress Report to the National Institute of Allergy and Infectious Diseases, Sep. 15, 1965 to Mar. 15, 1966, 21 pgs.

Melchers et al., "Cross-talk between orientation-dependent recognition determinants of a complex control RNA element, the enterovirus oriR". RNA, vol. 6, 2000, pp. 976-987.

Mendez et al., "Molecular Characterization of Transmissible Gastroenteritis Coronavirus Defective Interfering Genomes: Packaging and Heterogeneity". Virology, vol. 217, 1996, pp. 495-507.

Meng et al., "Characterization of a High-Virulence US Isolate of Porcine Reproductive and Respiratory Syndrome Virus in a Continuous Cell Line, ATCC CRL11171". Journal of Veterinary Diagnostic Investigation, vol. 8, No. 3, Jul. 1996, pp. 374-381.

Meng et al., "Molecular cloning and nucleotide sequencing of the 3'-terminal genomic RNA of the porcine reproductive and respiratory syndrome virus". Journal of General Virology, vol. 75, 1994, pp. 1795-1801.

Meng et al., "Phylogenetic analyses of the putative M (ORF 6) and N (ORF 7) genes of porcine reproductive and respiratory syndrome virus (PRRSV): implication for the existence of two genotypes of PRRSV in the U.S.A. and Europe". Archives of Virology, vol. 140, No. 4, 1995, pp. 745-755.

Meng, X.J., "Heterogeneity of porcine reproductive and respiratory syndrome virus: implications for current vaccine efficacy and future vaccine development". Veterinary Microbiology, vol. 74, 2000, pp. 309-329.

Mengeling et al., "An update of research at the National Animal Disease Center on current field strains of Porcine Reproductive and Respiratory Syndrome (PRRS) virus". Allen D. Leman Swine Conference, 1997, pp. 138-145.

Mengeling et al., "Clinical Effects of porcine reproductive and respiratory syndrome virus on pigs during the early postnatal interval". American Journal of Veterinary Research, vol. 59, No. 1, Jan. 1998, pp. 52-55.

Matanin et al., "Purification of the major envelop protein GP5 of porcine reproductive and respiratory syndrome virus (PRRSV) from native virions". Journal of Virological Methods, vol. 147, 2008, pp. 127-135.

Pesch et al., "New insights into the genetic diversity of European porcine reproductive and respiratory syndrome virus (PRRSV)". Veterinary Microbiology, vol. 107, 2005, pp. 31-48.

Darwich et al., "Genetic and immunobiological diversities of porcine reproductive and respiratory syndrome genotype I strains". Veterinary Microbiology, vol. 150, 2011, pp. 49-62.

UniProt: Accession No. C9E449. "SubName: Full=M protein; SubName: Full= Membrane protein". Nov. 3, 2009.

UniProt: Accession No. D0VEE4. "SubName: Full=Unglycosylated membrane protein". Dec. 15, 2009.

UniProt: Accession No. Q6TLB4. "SubName: Full= Membrane protein M". Jul. 5, 2004.

Wensvoort et al., "Mystery Swine Disease in the Netherlands the Isolation of Lelystad Virus". The Veterinary Quarterly, vol. 13, No. 3, 1991, pp. 121-130.

Wensvoort et al., "Production of Monoclonal Antibodies Against Swine Fever Virus and Their Use in Laboratory Diagnosis". Veterinary Microbiology, vol. 12, 1986, pp. 101-108.

Wensvoort et al., "The Porcine Reproductive and Respiratory Syndrome; Characteristics and diagnosis of the causative virus". Veterinary Biotechnology Newsletter, vol. 3, 1993, pp. 113-120.

Wesley et al., "Differentiation of vaccine (strain RespPRRS) and field strains of porcine reproductive and respiratory syndrome virus by restriction enzyme analysis". Proceedings of the American Association on Swine Practitioners, Nashville, TN, USA, 1996, pp. 141-143.

Westenbrink et al., "An enzyme-linked immunosorbent assay for detection of antibodies to porcine parvovirus". Journal of Virological Methods, vol. 23, 1989, pp. 169-178.

Wieczorek-Krohmer et al., "Porcine reproductive and respiratory syndrome virus (PRRSV): Monoclonal antibodies detect common epitopes on two viral proteins of European and U.S. isolates". Veterinary Microbiology, vol. 51, Nos. 3-4, Aug. 1996, pp. 257-266.

Witte, K.H. "The Situation of 'Epidemic Late Abortion of Swine' in the State of Northrhine-Westphalia". Workshop Seminar, Apr. 1991.

Woode, et al., "Porcine Rotavirus Infection". Diseases of Swine, Fifth Edition, Chapter 26, The Iowa State University Press, Ames, Iowa, 1981, pp. 310-322.

Woods et al., "Antigenicity of Inactivated Swine Influenza Virus Concentrated by Centrifugation". Research Communications in Chemical Pathology and Pharmacology, vol. 13, No. 1, 1976, pp. 129-132.

Woods et al., "Experimental challenge of pregnant gilts with swine influenza virus after vaccination". Research Communications in Chemical Pathology and Pharmacology, vol. 15, No. 4, Dec. 1976, pp. 787-795.

Woods et al., "Investigation of Four Outbreaks of Acute Respiratory Disease in Swine and Isolation of Swine Influenza Virus". Health Laboratory Science, vol. 5, No. 4, Oct. 1968, pp. 218-224.

Wootton et al., "Structure-function of the ORF7 protein of porcine reproductive and respiratory syndrome virus in the viral capsid assembly". Proceedings of the International Symposium on PRRS and Aujeszky's Disease, Ploufragan, France, pp. 37-38, (1999).

Yamane et al., "Annual Examination of Influenza Virus Infection Among Pigs in Miyagi Prefecture, Japan: The Appearance of Hsw1N1 Virus". Acta Virologica, vol. 23, 1979, pp. 240-248.

Yang et al., "Comparative sequence analysis of open reading frames 2 to 7 of the modified live vaccine virus and other North American isolates of the porcine reproductive and respiratory syndrome virus". Archives of Virology, vol. 143, 1998, pp. 601-612.

Yoon et al., "A modified serum neutralization test for the detection of antibody to porcine reproductive and respiratory syndrome virus in swine sera". Journal of Veterinary Diagnostic Investigation, vol. 6, No. 3, Jul. 1994, pp. 289-292.

Yoon et al., "Failure to Consider the Antigenic Diversity of Porcine Reproductive and Respiratory Syndrome (PRRS) Virus Isolates May Lead to Misdiagnosis". Journal of Veterinary Diagnostic Investigation, vol. 7, Jul. 1995, pp. 386-387.

Yoon et al., "Isolation of a Cytopathic Virus from Weak Pigs on Farms with a History of Swine Infertility and Respiratory Syndrome". Journal of Veterinary Diagnostic Investigation, vol. 4, Apr. 1992, pp. 139-143.

Yu et al., "Specific Binding of Host Cellular Proteins to Multiple Sites within the 39 End of Mouse Hepatitis Virus Genomic RNA". Journal of Virology, vol. 69, No. 4, Apr. 1995, pp. 2016-2023.

Yuan et al., "Complete genome comparison of porcine reproductive and respiratory syndrome virus parental and attenuated strains". Virus Research, vol. 74, 2001, pp. 99-110.

Yuan et al., "Erratum to 'Complete genome comparison of porcine reproductive and respiratory syndrome virus parental and attenuated strains '[Virus Research 74 (2001) 99-110]". Virus Research, vol. 79, 2001, p. 187.

Yuan et al., "Molecular characterization of a highly pathogenic strain of PRRSV associated with porcine High Fever syndrome in China". 2007 International Porcine Reproductive and Respiratory Syndrome (PRRS) Symposium, Chicago, Illinois, Nov.-Dec. 2007, Poster 70.

Yuan et al., American Society for Virology, 16th Annual Meeting, Bozeman, Montana, Jul. 19-23, 1997, Abstract P29-5, p. 229.

Zeijst, et al., "The Genome of Equine Arteritis Virus". Virology, vol. 68, 1975, pp. 418-425.

Zhou et al., "Generation of cytotoxic and humoral immune responses by nonreplicative recombinant Semliki Forest virus". Proceedings of the National Academy of Sciences, vol. 92, Mar. 1995, pp. 3009-3013.

Zimmerman et al., "General overview of PRRSV: a perspective from the United States". Veterinary Microbiology, vol. 55, Nos. 1-4, Apr. 1997, pp. 187-196.

Carvajal et al., "Evaluation of a Blocking ELISA Using Monoclonal Antibodies for the Detection of Porcine Epidemic Diarrhea Virus and Its Antibodies". Journal of Veterinary Diagnostic Investigation, vol. 7, No. 1, Jan. 1995, pp. 60-64.

Cavanagh, D., "Nidovirales: a new order comprising Coronaviridae and Arteriviridae". Archives of Virology, vol. 142, No. 3, 1997, pp. 629-633.

Chang et al., "A cis-Acting Function for the Coronavirus Leader in Defective Interfering RNA Replication". Journal of Virology, vol. 68, No. 12, Dec. 1994, pp. 8223-8231.

Chang et al., "Evolution of Porcine Reproductive and Respiratory Syndrome Virus during Sequential Passages in Pigs". Journal of Virology, vol. 76, No. 10, May 2002, pp. 4750-4763.

Chao et al., "Monoclonal Antibodies to Metacyclic Stage Antigens of Trypanosoma Cruzi" The American Journal of Tropical Medicine and Hygiene, vol. 34, No. 4, Jul. 1985, pp. 694-701.

Charley, B., "Interaction of influenza virus with swine alveolar macrophages: Influence of anti-virus antibodies and cytochalasin B". Annales de l'Instiut Pasteur. Virologie, vol. 134, No. 1, Jan. 1983, pp. 51-59.

Chasey et al., "Replication of Atypical Ovine Rotavirus in Small Intestine and Cell Culture". Journal of General Virology, vol. 67, No. 3, Mar. 1986, pp. 567-576.

Chen et al., "Determination of the 5' end of the lactate dehydrogenase-elevating virus genome by two independent approaches". Journal of General Virology, vol. 75, 1994, pp. 925-930.

Christianson et al., "Experimental Reproduction of a Newly Described Viral Disease, Swine Infertility and Respiratory Syndrome (SIRS), in Pregnant Sows". 72nd Annual Meeting of the Conference of Research Workers in Animal Disease, Chicago, IL, Nov. 11 & 12, 1991, p. 48, Abstract No. 269.

Christianson et al., "Experimental reproduction of swine infertility and respiratory syndrome in pregnant sows". American Journal of Veterinary Research, vol. 53, No. 4, Apr. 1992, pp. 485-488.

Christianson et al., "Porcine reproductive and respiratory syndrome: a review"., Journal of Swine Health and Production, vol. 2, No. 2, Mar. and Apr. 1994, pp. 10-28.

Christianson et al., "Swine Infertility and Respiratory Syndrome". Pig Veterinary Journal, vol. 27, No. 9, Apr. 1991, pp. 9-12.

Chutivongse et al., "One-year study of the 2-1-1 intramuscular postexposure rabies vaccine regimen in 100 severely exposed Thai patients using rabies immune globulin and Vero cell rabies vaccine". Vaccine, vol. 9, No. 8, Aug. 1991, pp. 573-576.

Clark et al., "Trypsin enhancement of rotavirus infectivity: mechanism of enhancement". Journal of Virology, vol. 39, No. 3, Sep. 1981, pp. 816-822.

Collins et al., "Experimental Transmission of Swine Reproductive Failure Syndrome (Mystery Swine Disease) in Gnotobiotic Piglets". 71st Annual Meeting of the Conference of Research Workers in Animal Disease, Chicago, IL, Nov. 5-6, 1990, Abstract No. 2.

Collins et al., "Isolation of swine infertility and respiratory syndrome virus (isolate ATCC VR-2332) in North America and experimental reproduction of the disease in gnotobiotic pigs". Journal of Veterinary Diagnostic Investigation, vol. 4, 1992, pp. 117-126.

Collins et al., "Production of infectious human respiratory syncytial virus from cloned cDNA confirms an essential role for the transcription elongation factor from the 5' proximal open reading frame of the M2 mRNA in gene expression and provides a capability for vaccine development". Proceedings of the National Academy of Sciences, vol. 92, Dec. 1995, pp. 11563-11567.

Collins et al., "Respiratory Disease in a Swine Herd Experiencing a Reproductive Failure Syndrome". Minnesota Swine Conference for Veterinarians, Sep. 16-18, 1990, pp. 206-207.

Collins et al., "Swine Diagnostic Pathology". Allen D. Leman Swine Conference, College of Veterinary Medicine, University of Minnesota, Sep. 18-22, 1998, pp. 1-4.

Collins et al., "Swine Infertility and Respiratory Syndrome (Mystery Swine Disease)". Minnesota Swine Conference for Veterinarians, St. Paul, MN, Sep. 15-17, 1991, pp. 200-205.

Collins, J.E., "Newly Recognized Respiratory Syndromes in North American Swine Herds". American Association of Swine Practitioners Newsletter, vol. 3, No. 7, Sep.-Oct. 1991, pp. 7, 10-11.

Conner et al., "Isolation and characteristics of an equine reovirus type 3 and an antibody prevalence survey to reoviruses in horses located in New York State". Veterinary Microbiology, vol. 9, No. 1, Feb. 1984, pp. 15-25.

Conzelmann et al., "Molecular Characterization of Porcine Reproductive and Respiratory Syndrome Virus, a Member of the Arterivirus Group". Virology, vol. 193, 1993, pp. 329-339.

Cooper et al., "Porcine Reproductive and Respiratory Syndrome: NEB-1 PRRSV Infection did not Potentiate Bacterial Pathogens". Journal of Veterinary Diagnostic Investigation, vol. 7, No. 3, Jul. 1995, pp. 313-320.

Corn et al., "Isolation of Vesicular Stomatitis Virus New Jersey Serotype from Phlebotomine Sand Files in Georgia". The American Journal of Tropical Medicine and Hygiene, vol. 42, No. 5, May 1990, pp. 476-482.

Dacso, et al., "Sporadic occurrence of zoonotic swine influenza virus infections". Journal of Clinical Microbiology, vol. 20, No. 4, Oct. 1984, pp. 833-835.

Database WPIL Week 8702, Derwent Publications Ltd., London, GB; AN 87-009295 [2] & EP, A,208672 (Regional Wallonne-Chiron Corp, Wallonne Regional) Jan. 14, 1987.

Database WPIL Week 8741, Derwent Publications Ltd., London, GB; AN 87-286929 [41] & EP, A,62, 198626 (ZA Bieseibutsu Kagaku Ken) Sep. 2, 1987.

Database WPIL Week 8821, Derwent Publications Ltd., London, GB; AN 88-147502 [21] & WO,A,8 803 410 (Inst Pasteur) May 19, 1988.

De Mazancourt et al., "Antibody response to the rubella virus structural proteins in infants with the congenital rubella syndrome". Journal of Medical Virology, vol. 19, No. 2, Jun. 1986, pp. 111-122.

De Vries et al., "Genetic Manipulation of Equine Arteritis Virus Using Full-Length cDNA Clones: Separation of Overlapping Genes and Expression of a Foreign Epitope". Virology, vol. 270, No. 1, 2000, pp. 84-97.

De Vries et al., "The Genome Organization of the Nidovirales: Similarities and Differences between Arteri-, Toro-, and Coronaviruses". Seminars in Virology, vol. 8, 1997, pp. 33-47.

De Vries, et al., "All subgenomic mRNAs of equine arteritis virus contain a common leader sequence". Nucleic Acids Research, vol. 18, No. 11, 1990, pp. 3241-3247.

Dea et al., "Antigenic Variability among North American and European Strains of Porcine Reproductive and Respiratory Syndrome Virus as Defined by Monoclonal Antibodies to the Matrix Protein". Journal of Clinical Microbiology, vol. 34, No. 5, Jun. 1996, pp. 1488-1493.

Dea et al., "Antigenic variant of swine influenza virus causing proliferative and necrotizing pneumonia in pigs". Journal of Veterinary Diagnostic Investigation, vol. 4, No, 4, 1992, pp. 380-392.

Dea et al., "Caracteristiques d'Isolats des virus influenza et de l'encephalomyocardite associes au Syndrome Reproducteur et Respiratoire Porcine (S.R.R.P.) au Quebec.sup.a," Le Medecin Veterinaire Du Quebec, vol. 21, No. 4, Nov. 1991, pp. 170-175.

Dea et al., "Current knowledge on the structural proteins of porcine reproductive and respiratory syndrome (PRRS) virus: comparison of the North American and European isolate". Archives of Virology, vol. 145, No. 4, Apr. 2000, pp. 659-688.

Dea et al., "Isolation of encephalomyocarditis virus among stillborn and post-weaning pigs in Quebec". Archives of Virology, vol. 117, Nos. 1-2, 1991, pp. 121-128.

Dea et al., "Swine reproductive and respiratory syndrome in Quebec: Isolation of an enveloped virus serologically-related to Lelystad virus". Canadian Veterinary Journal, vol. 33, No. 12, Dec. 1992, pp. 801-808.

Dea et al., "Virus Isolations from Farms in Quebec Experiencing Severe Outbreaks of Respiratory and Reproductive Problems". Proceedings of the Mystery Swine Disease Committee Meeting, Denver, CO, Oct. 6, 1990, pp. 67-72.

Del Val et al., "Glycosylated components of African swine fever virus particles". Virology, vol. 152, No. 1, Jul. 1986, pp. 39-49.

Den Boon et al., "Equine Arteritis Virus Is Not a Togavirus but Belongs to the Coronaviruslike Superfamily". Journal of Virology, vol. 65, No. 6, 1991, pp. 2910-2920.

Den Boon et al., "Processing and Evolution of the N-Terminal Region of the Arterivirus Replicase ORF1a Protein: Identification of Two Papainlike Cysteine Proteases". Journal of Virology, vol. 69, No. 7, Jul. 1995, pp. 4500-4505.

Deng et al., "An improved procedure for utilizing terminal transferase to add homopolymers to the 3' termini of DNA". Nucleic Acids Research, vol. 9, No. 16, 1981, pp. 4173-4188.

Derbyshire, J.B. "Porcine Enterovirus Infections". Diseases of Swine, Fifth Edition, Chapter 20, 1981, pp. 265-270.

Devereux et al., "A Comprehensive Set of Sequence Analysis Programs for VAX". Nucleic Acids Research, vol. 12, No. 1, 1984, pp. 387-395.

Dianzani et al., "Is Human Immunodeficiency Virus RNA Load Composed of Neutralized Immune Complexes". The Journal of Infectious Diseases, vol. 185, 2002, pp. 1051-1054.

Dildrop et al., "Immunoglobulin V region variants in hybridoma cells. II. Recombination between V genes". The EMBO Journal, vol. 1, No. 5, 1982, pp. 635-640.

Dreher, T.W., "Functions of the 3'-Untranslated Regions of Positive Strand RNA Viral Genomes". Annual Review of Phytopathology, vol. 37, 1999, pp. 151-174.

Drew et al., "Production, characterization and reactivity of monoclonal antibodies to porcine reproductive and respiratory syndrome virus". Journal of General Virology, vol. 76, 1995, pp. 1361-1369.

Mengeling et al., "Comparative safety and efficacy of attenuated single-strain and multi-strain vaccines for porcine reproductive and respiratory syndrome". Veterinary Microbiology, vol. 93, 2003, pp. 25-38.

Mengeling et al., "Comparison among strains of porcine reproductive and respiratory syndrome virus for their ability to cause reproductive failure". American Journal of Veterinary Research, vol. 57, No. 6, Jun. 1996, pp. 834-839.

Mengeling et al., "Mystery Pig Disease: Evidence and Considerations for its Etiology". Proceedings of the Mystery Swine Disease Committee Meeting, Oct. 6, 1990, Denver, Colorado, Livestock Conservation Institute, Madison, WI, USA, pp. 88-90.

Mengeling et al., "Strain specificity of the immune response of pigs following vaccination with various strains of porcine reproductive and respiratory syndrome virus". Veterinary Microbiology, vol. 93, 2003, pp. 13-24.

Meredith, MJ, "Porcine Reproductive and Respiratory Syndrome (PRRS)", Pig Disease Information Center, 1st North American Edition, University of Cambridge, Aug. 1994, pp. 1-57.

Mettenleiter et al., "Isolation of a viable herpesvirus (pseudorabies virus) mutant specifically lacking all four known nonessential glycoproteins". Virology, vol. 179, No. 1, Nov. 1990, pp. 498-503.

Meulenberg et al., "An infectious cDNA clone of Porcine Reproductive and Respiratory Syndrome Virus". Coronaviruses and Arteriviruses (Advances in Experimental Medicine and Biology, vol. 440), Ch. 24, 1998, pp. 199-206.

Meulenberg et al., "Characterization of Proteins Encoded by ORFs 2 to 7 of Lelystad Virus". Virology, vol. 206, No. 1, Jan. 1995, pp. 155-163.

Meulenberg et al., "Identification and Characterization of a Sixth Structural Protein of Lelystad Virus: The Glycoprotein GP2Encoded by ORF2 Is Incorporated in Virus Particles". Virology, vol. 225, No. 1, Nov. 1996, pp. 44-51.

Meulenberg et al., "Infectious Transcripts from Cloned Genome-Length cDNA of Porcine Reproductive and Respiratory Syndrome Virus". Journal of Virology, vol. 72, No. 1, Jan. 1998, pp. 380-387.

Meulenberg et al., "Lelystad Virus, the Causative Agent of Porcine Epidemic Abortion and Respiratory Syndrome (PEARS), is Related to LDV and EAV". Virology, vol. 192, 1993, pp. 62-72.

Meulenberg et al., "Localization and Fine Mapping of Antigenic Sites on the Nucleocapsid Protein N of Porcine Reproductive and Respiratory Syndrome Virus with Monoclonal Antibodies". Virology, vol. 252, 1998, pp. 106-114.

Meulenberg et al., "Molecular characterization of Lelystad virus". Veterinary Microbiology, vol. 55, 1997, pp. 197-202.

Meulenberg et al., "Nucleocapsid Protein N of Lelystad Virus: Expression by Recombinant Baculovirus, Immunological Properties, and Suitability for Detection of Serum Antibodies". Clinical and Diagnostic Laboratory Immunology, vol. 2, No. 6, Nov. 1995, pp. 652-656.

Meulenberg et al., "Posttranslational Processing and Identification of a Neutralization Domain of the GP4 Protein Encoded by ORF4 of Lelystad Virus". Journal of Virology, vol. 71, No. 8, Aug. 1997, pp. 6061-6067.

Meulenberg et al., "Subgenomic RNAs of Lelystad virus contain a conserved leader-body junction sequence". Journal of General Virology, vol. 74, 1993, pp. 1697-1701.

Molenkamp et al., "Isolation and Characterization of an Arterivirus Defective Interfering RNA Genome". Journal of Virology, vol. 74, No. 7, 2000, pp. 3156-3165.

Molenkamp et al., "The arterivirus replicase is the only viral protein required for genome replication and subgenomic mRNA transcription". Journal of General Virology, vol. 81, No. 10, 2000, pp. 2491-2496.

Montagnon, B.J., "Polio and rabies vaccines produced in continuous cell lines: a reality for Vero cell line". Dev Biol Stand., vol. 70, 1989, pp. 27-47.

Moore, C., "Porcine Proliferative and Necrotyzing Pneumonia Clinical Findings". Presented at American Association of Swine Practitioners, 22nd Annual Meeting, Mar. 3-5, 1991, pp. 443-453.

Moormann et al., "Hog cholera virus: identification and characterization of the viral RNA and the virus specific RNA synthesized in infected swine kidney cells". Virus Research, vol. 11, 1988, pp. 281-291.

Moormann et al., "Infectious RNA Transcribed from an Engineered Full-Length cDNA Template of the Genome of a Pestivirus". Journal of Virology, vol. 70, No. 2, Feb. 1996, pp. 763-770.

Moormann et al., "Molecular cloning and nucleotide sequence of hog cholera virus strain brescia and mapping of the genomic region encoding envelope protein E1". Virology, vol. 177, No. 1, Jul. 1990, pp. 184-198.

Morin et al., "Severe proliferative and necrotizing pneumonia in pigs: a newly recognized disease". Canadian Veterinary Journal, vol. 31, Dec. 1990, pp. 837-839.

Morozov et al., "Sequence analysis of open reading frames (ORFs) 2 to 4 of a U.S. isolate of porcine reproductive and respiratory syndrome virus". Archives of Virology, vol. 140, No. 7, 1995, pp. 1313-1319.

Morrison et al., "Brief Communications Serologic evidence incriminating a recently isolated virus (ATCC VR-2332) as the cause of swine infertility and respiratory syndrome (SIRS)". Journal of Veterinary Diagnostic Investigation, vol. 4, No. 2, Apr. 1992, pp. 186-188.

Morrison et al., "Sero-epidemiologic Investigation of Swine Infertility and Respiratory Syndrome (SIRS)". 72st Annual Meeting of the Conference of Research Workers in Animal Disease, Chicago, IL, Nov. 11-12, 1991, p. 55, Abstract No. 309.

Mountz et al., "The in vivo generation of murine IgD-secreting cells is accompanied by deletion of the Cμ gene and occasional deletion of the gene for the Cd1 domain". The Journal of Immunology, vol. 145, No. 5, Sep. 1990, pp. 1583-1591.

Mukamoto et al., "Immunogenicity in Aujeszky's disease virus structural glycoprotein gVl (gp50) in swine". Veterinary Microbiology, vol. 29, No. 2, Oct. 1991, pp. 109-121.

Murakami, et al., "Difference in growth behavior of human, swine, equine, and avian influenza viruses at a high temperature". Archives of Virology, vol. 100, Nos. 3-4, 1988, pp. 231-244.

Murphy et al., "Immunization Against Virus" in Virology, 2nd Edition, vol. 1, Fields, et al., eds. Raven Press, NY, 1990, pp. 469-502.

Murphy et al., "Virus Taxonomy". Chapter 2 in Fields Virology, 2nd. Edition, Fields, et al., eds, Raven Press, New York, 1990, pp. 9-35.

Murtaugh et al., "Comparison of the structural protein coding sequences of the VR-2332 and Lelystad virus strains of the PRRS virus". Archives of Virology, vol. 140, No. 8, 1995, pp. 1451-1460.

Murtaugh et al., "Genetic Variation in the PRRS Virus". Coronaviruses and Arteriviruses, Plenum Press, New York, 1998, pp. 787-794.

Murtaugh et al., "Immunological Responses of Swine to Porcine Reproductive and Respiratory Syndrome Virus Infection". Viral Immunology, vol. 15, No. 4, 2002, pp. 533-547.

Murtaugh et al., "Role of Viral Proteases in PRRS Immunity, Project Period Sep. 1, 1997-Dec. 31, 2002, no cost extension Jan. 1, 2003-Jun. 30, 2003". Final Report: Aug. 30, 2003, Department of Veterinary Pathology, University of Minnesota, St. Paul, MN and Boehringer Ingelheim Vetmedica, Inc., Ames, IA, 2003, pp. 1-38.

Murtaugh, "Allen D Lehman Swine Conference: the Evolution of the Swine veterinary profession: the PRRS Virus". University of Minnesota, Veterinary Continuing Education and Extension, vol. 20, 1993, pp. 43-47.

Myers et al., "Propagation of avian rotavirus in primary chick kidney cell and MA104 cell cultures". Avian Diseases, vol. 33, No. 3, Jul.-Sep. 1989, pp. 578-581.

Nakamura et al., "Studies on Swine Influenza III. Propagation of Swine Influenza Virus in Explants of Respiratory Tract Tissues from Fetal Pigs". The Cornell Veterinarian, vol. LX, No. 1, Jan. 1970, pp. 27-35.

Narayanan et al., "Characterization of the Coronavirus M Protein and Nucleocapsid Interaction in Infected Cells". Journal of Virology, vol. 74, No. 17, Sep. 2000, pp. 8127-8134.

NCBI: Accession No. AE005172. "*Arabidopsis thaliana* chromosome 1, top arm complete sequence." Dec. 14, 2000.

NCBI: Accession No. AF046869. "Porcine reproductive and respiratory syndrome virus isolate 16244B, Feb. 28, 1997 (Nebraska) pass.3, complete genome." Mar. 17, 1999.

NCBI: Accession No. AF066183. "Porcine reproductive and respiratory syndrome virus RespPRRS MLV, complete genome." Feb. 22, 2001.

NCBI: Accession No. AF159149. "Porcine reproductive and respiratory syndrome virus isolate MLV RespPRRS/Repro, complete genome." Aug. 28, 2000.

NCBI: Accession No. AF176348. "Porcine reproductive and respiratory syndrome virus isolate PA8 complete genome." Sep. 3, 2002.

NCBI: Accession No. AF184212. "Porcine reproductive and respiratory syndrome virus strain SP, complete genome." Sep. 28, 2000.

NCBI: Accession No. AF325691. "Porcine reproductive and respiratory syndrome virus isolate NVSL 977985 IA 1-4-2, complete genome." Feb. 11, 2001.

NCBI: Accession No. AF331831. "Porcine reproductive and respiratory syndrome virus BJ-4, complete genome." Jan. 15, 2001.

NCBI: Accession No. M96262. "Lelystad virus, complete genome." Nov. 8, 2000.

NCBI: Accession No. M96262.2. "Lelystad virus, complete genome." Nov. 8, 2000.

NCBI: Accession No. NC_001639. Lactate dehydrogenase-elevating virus, complete genome. Dec. 8, 2008.

NCBI: Accession No. NC_001961. "Porcine reproductive and respiratory syndrome virus, complete genome." Jan. 12, 2004.

NCBI: Accession No. NC_002533. "Lelystad virus, complete genome." Nov. 11, 2000.

NCBI: Accession No. NC_002534. "Lactate dehydrogenase-elevating virus, complete genome." Dec. 29, 2003.

NCBI: Accession No. U15146. "Lactate dehydrogenase-elevating virus Plagemann strain, complete genome." Jan. 26, 1996.

NCBI: Accession No. U87392 AF030244 000153. "Porcine reproductive and respiratory syndrome virus strain VR-2332, complete genome." Nov. 17, 2000.

Nelsen et al., "Porcine Reproductive and Respiratory Syndrome Virus Comparison: Divergent Evolution on Two Continents". Journal of Virology, vol. 73, No. 1, Jan. 1999, pp. 270-280.

Nelson et al., "Differentiation of U.S. and European Isolates of Porcine Reproductive and Respiratory Syndrome Virus by Monoclonal Antibodies". Journal of Clinical Microbiology, vol. 31, No. 12, Dec. 1993, pp. 3184-3189.

Nelson et al., "High affinity interaction between nucleocapsid protein and leader/intergenic sequence of mouse hepatitis virus RNA". Journal of General Virology, vol. 81, 2000, pp. 181-188.

Nielsen et al., "Generation of an Infectious Clone of VR-2332, a Highly Virulent North American-Type Isolate of Porcine Reproductive and Respiratory Syndrome Virus". Journal of Virology, vol. 77, No. 6, Mar. 2003, pp. 3702-3711.

Nishimura et al., "Replication and Synthesis of Japanese Encephalitis Virus Ribonucleic Acids in Vero Cells". Japanese Journal of Microbiology, vol. 15, No. 4, 1971, pp. 309-316.

Nodelijk et al., "A quantitative assessment of the effectiveness of PRRSV vaccination in pigs under experimental conditions". Vaccine, vol. 19, 2000, pp. 3636-3644.

Nuttall, P.A., "Growth Characteristics of Two Strains of Bovine Virus Diarrhoea Virus". Archives of Virology, vol. 66, 1980, pp. 365-369.

Oirschot et al., "Development of an ELISA for detection of antibodies to glycoprotein I of Aujeszky's disease virus: a method for the serological differentiation between infected and vaccinated pigs". Journal of Virological Methods, vol. 22, 1988, pp. 191-206.

Ojeh et al., "Isolation, characterisation and serial propagation of a Nigerian strain of porcine group A rotavirus in a monkey kidney cell line (MA104)". Discovery and Innovation, vol. 8, No. 2, Jun. 1996, pp. 159-164.

Oleksiewicz et al., "Epitope Mapping Porcine Reproductive and Respiratory Syndrome Virus by Phage Display: the nsp2 Fragment of the Replicase Polyprotein Contains a Cluster of B-Cell Epitopes". Journal of Virology, vol. 75, No. 7, Apr. 2001, pp. 3277-3290.

Oleksiewicz et al., "Semen from Boars Infected with Porcine Reproductive and Respiratory Syndrome Virus (PRRSV) Contains Antibodies Against Structural as Well as Nonstructural Viral Proteins". Veterinary Microbiology, vol. 81, 2001, pp. 109-125.

Olsthoorn et al., "A conformational switch at the 3' end of a plant virus RNA regulates viral replication". The EMBO Journal, vol. 18, No. 17, 1999, pp. 4856-4864.

Opriessnig et al., "Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and Two Recent Field Isolates of PRRSV". Journal of Virology, vol. 76, No. 23, Dec. 2002, pp. 11837-11844.

Ostrowski et al., "Identification of Neutralizing and Nonneutralizing Epitopes in the Porcine Reproductive and Respiratory Syndrome Virus GP5 Ectodomain". Journal of Virology, vol. 76, No. 9, May 2002, pp. 4241-4250.

Pan et al., "Replication of African swine fever virus in cell cultures". American Journal of Veterinary Research, vol. 41, No. 9, Sep. 1980, pp. 1357-1367.

Parratt et al., "Radioimmunoassay of Antibody and its Clinical Applications". John Wiley & Sons, Chichester, 1982, p. 43.

Parsley et al., "Poly (rC) binding protein 2 forms a ternary complex with the 5'-terminal sequences of poliovirus RNA and the viral 3CD proteinase". RNA, vol. 3, 1997, pp. 1124-1134.

Patriarca, et al., "Lack of Significant Person-to-Person Spread of Swine Influenza-Like Virus Following Fatal Infection in an Immunocomprised Child". American Journal of Epidemiology, vol. 119, No. 2, 1984, pp. 152-158.

Paul et al., "Porcine Reproductive and Respiratory Syndrome: An Overview". Journal of Clinical Veterinary Medicine, vol. 11, No. 12, Nov. 1993, pp. 1-16.

Pearson et al., "Improved tools for biological sequence comparison". Proceedings of the National Academy of Sciences, vol. 85, Apr. 1988, pp. 2444-2448.

Pedersen et al., "Open Reading Frame 1a-Encoded Subunits of the Arterivirus Replicase Induce Endoplasmic Reticulum-Derived Double-Membrane Vesicles Which Carry the Viral Replication Complex". Journal of Virology, vol. 73, No. 3, Mar. 1999, pp. 2016-2026.

Pejsak et al., "Clinical signs and economic losses caused by porcine reproductive and respiratory syndrome virus in a large breeding farm". Veterinary Microbiology, vol. 44, 1997, pp. 317-322.

Peng et al., "Analysis of Second-Site Revertants of a Murine Coronavirus Nucleocapsid Protein Deletion Mutant and Construction of Nucleocapsid Protein Mutants by Targeted RNA Recombination". Journal of Virology, vol. 69, No. 6, Jun. 1995, pp. 3449-3457.

Penzes et al., "Characterization of a Replicating and Packaged Defective RNA of Avian Coronavirus Infectious Bronchitis Virus". vol. 203, No. 2, Sep. 1994, pp. 286-293.

Percy et al., "Expression of a Foreign Protein by Influenza A Virus". Journal of Virology, vol. 68, No. 7, Jul. 1994, pp. 4486-4492.

Pirtle et al., "Morphologic Heterogeneity of a Strain of Swine Influenza Virus (A/Swine/Wisconsin/1/68, Hsw1N1) Propagated at Different Temperatures". American Journal of Veterinary Research, vol. 36, No. 1, 1975, pp. 1783-1787.

Plagemann et al., "Lactate Dehydrogenase-Elevating Virus, Equine Arteritis Virus, and Simina Hemorrhagic Fever Virus: A New Group of Positive-Strand RNA Viruses". Advances in Virus Research, vol. 41, 1991, pp. 99-192.

Pol et al., "Pathological, ultrastructural, immunohistochemical changes caused by Lelystad virus in experimentally induced infections of mystery swine disease (synonym: porcine epidemic abortion and respiratory syndrome (PEARS))". Veterinary Quarterly, vol. 13, No. 3, Jul. 1991, pp. 137-143.

Polson et al., "An evaluation of the financial impact of Porcine Reproductive and Respiratory Syndrome (PRRS) in nursery pigs". Proceedings of the 13th International Pig Veterinary Society Congress, Jun. 1994, p. 31.

Polson et al., "Financial Implications of Mystery Swine Disease (MSD)". 1993, pp. 8-28.

Polson, DD, "Answers to Your Questions on PRRS". NOBL Laboratories, 1993, 18 Pages.

Polson, DD, "RespPRRS a PRRS Vaccine Review", NOBL Laboratories, 1993, 22 pages.

Porcine Reproductive and Respiratory Syndrome: A Report on the Seminar Held in Brussels on Nov. 4-5, 1991 and Organized by the European Commission.

Poser, C.M., "Swine Influenza Vaccination: Truth and Consequences". Archives of Neurology, vol. 42, No. 11, 1985, pp. 1090-1092.

Potgieter et al., "Isolation of Swine Influenza Virus in Oklahoma". Journal of the American Veterinary Medical Association, vol. 171, No. 8, 1977, pp. 758-760.

Potts et al., "Peroxidase-labeled primary antibody method for detection of pestivirus contamination in cell cultures". Journal of Virological Methods, vol. 26, No. 1, Oct. 1989, pp. 119-124.

Quaife, T. "Mystery Agent Isolated! Isolation of the etiological agent behind mystery swine disease is a major breakthrough". Swine Practitioner, Mystery Disease: Part 8, Nov. 1991, pp. 4-7.

Reed et al., "A Simple Method of Estimating Fifty Per Cent Endpoints"., The American Journal of Hygiene, vol. 27, No. 3, May 1938, pp. 493-497.

Reed et al., "Persistent Respiratory Virus Infection in Tracheal Organ Cultures". British Journal of Experimental Pathology, vol. 50, 1969, pp. 378-388.

Rice et al., "Production of Infectious RNA Transcripts from Sindbis Virus cDNA Clones: Mapping of Lethal Mutations, Rescue of a Temperature-Sensitive Marker, and In Vitro Mutagenesis to Generate Defined Mutants". Journal of Virology, vol. 61, No. 12, Dec. 1987, pp. 3809-3819.

Roberts et al., "Abortion in Swine". Veterinary Ostetrics and Genital Diseases, Edwards Brothers, Inc., Ann Arbor, 1986, pp. 180-192.

Roof et al., "Efficacy of Modified Live Virus Porcine Reproductive and Respiratory Virus Vaccines Against Heterologous Respiratory Challenge". 4th International Symposium on Emerging and Re-emerging Pig Diseases, Rome, Jun. 28-Jul. 2, 2003, pp. 117-118.

Ropp et al., "Characterization of Emerging European-Like Porcine Reproductive and Respiratory Syndrome Virus Isolates in the United States"., Journal of Virology, vol. 78, No. 7, Apr. 2004, pp. 3684-3703.

Rossow et al., "Experimental porcine reproductive and respiratory syndrome virus infection in one-, four-, and 10-week-old pigs". Journal of Veterinary Diagnostic Investigation, vol. 6, 1993, pp. 3-12.

* cited by examiner

PORCINE REPRODUCTIVE AND RESPIRATORY SYNDROME ISOLATES AND METHODS OF USE

The present application is filed as a continuation application of U.S. patent application Ser. No. 12/548,597, which was filed Aug. 27, 2009, as a continuation application of U.S. patent application Ser. No. 11/022,262 (now U.S. Pat. No. 7,632,636), which was filed Dec. 23, 2004, claiming the benefit of priority to U.S. Patent Application No. 60/611,824, which was filed on Sep. 21, 2004. The entire text of the aforementioned applications is incorporated herein by reference in its entirety.

BACKGROUND OF THE INVENTION

1. Field of the Invention

The present invention is concerned with new isolated wild-type PRRS virus strains and corresponding improved attenuated PRRS viruses, as well as methods of measuring the magnitude of viremia, rate of growth, antibody response, and combinations thereof in such strains and viruses. More particularly, the present invention provides methods for predicting the virulence of new or previously uncharacterized PRRS strains.

2. Description of the Prior Art

Porcine reproductive and respiratory syndrome virus (PRRSV) is an enveloped single stranded RNA virus classified in the family Arteriviridae (Cavanaugh, 1997). It causes a widespread disease of swine that was first described as 'mystery swine disease' in the USA in 1987 (Hill, 1990). The disease manifests as respiratory illness in all age groups of swine leading to death in some younger pigs and severe reproductive problems in breeding age females.

The dynamic nature of PRRSV allows for constant change in the disease and provides ample opportunity for the appearance of new strains (Andreyev et al., 1997; Murtaugh et al. 1998; Meng, 2000). The fact that PRRSV changes so readily, coupled with its ability to cause devastating problems for swine producers, makes it an important subject for research (Mengeling et al., 1998; Pejsak et al., 1997) and for the development of vaccines and other methods of reducing the effects of infection. Variation in levels of isolate virulence were demonstrated in lung lesions, and death in swine (Halbur et al., 1996), but efforts to link biological and immunological differences to specific genetic differences has been largely unsuccessful (Albina et al., 1998; Key et al., 2001; Yuan et al., 2001; Murtaugh et al., 2002; Grebennikova et al., 2004). Studies examining the safety and efficacy of PRRS vaccines include the work of Labarque et al., (2003), Mengeling et al., (2003a), and Nodelijik et al. (2001). These studies show that under experimental conditions, modified live PRRS vaccines reduce the amount and duration of viremia as well as fever and lung lesions after virulent challenge.

Opriessing et al. (2002) showed that isolates with high amino acid sequence homology in open reading frame 5 (ORF5) caused significantly different levels of pneumonia in pigs. Variation in swine responses to PRRSV also are affected by host variation (Mengeling et al., 2003b). Virulence has been examined in relation to replication rates and distribution of PRRSV in pigs (Haynes et al., 1997), to macrophage copper clearing capabilities (Thanawongnuwech et al., 1998), and the anemia levels of the host animal (Halbur et al, 2002). However, these methods have been deficient in providing effective methods for predicting the virulence of new or previously uncharacterized PRRS strains.

Accordingly, what is needed in the art is a method of predicting the virulence of PRRS strains. What is further needed in the art is a method of predicting the virulence of PRRS strains based on the rate of in vivo PRRS viral growth and/or viremia magnitude in a swine after administration or exposure of the strain to a previously PRRS-free swine.

SUMMARY OF THE INVENTION

The present invention overcomes the problems outlined above and provides methods for predicting the degree of virulence of a new or uncharacterized PRRS virus strain. The methods generally involve assessing a new or previously uncharacterized strain of PRRS for at least one of the following parameters: rate of viral growth; magnitude of viremia; antibody response; or combinations thereof. The results of such an assessment are then used to predict the degree of virulence of the new or previously uncharacterized strain. The methods generally involve administering or exposing a PRRS-free swine to a quantity of the new or uncharacterized PRRS strain and allowing the virus to replicate for a period of up to about 15 days, more preferably from about 2-12 days, still more preferably from about 3-10 days and still more preferably from about 3-7 days. The mode of administration can be accomplished using any conventional manner, including oral, intranasal, intramuscular, intra-lymph node, intradermal, intraperitoneal, subcutaneous, and combinations thereof, but most preferably through intranasal administration. The amount of the dose for intranasal administration is preferably up to about 5 ml, still more preferably between about 0.5 ml to about 4 ml, still more preferably between about 1 ml and about 3 ml, and still more preferably about 2 ml. The concentration of virus in each dose should be up to about 5.0 $Log_{10}$ $TCID_{50}$/ml, more preferably between about 1.0 to about 4.0 $Log_{10}$ $TCID_{50}$/ml, and still more preferably about 2.5 to 3.5 $Log_{10}$ $TCID_{50}$/ml, and most preferably about 3.0 $Log_{10}$ $TCID_{50}$/ml. At a selected time or times during this replication period, biological samples are taken from the swine and measurements of the rate of growth of the administered virus, viremia magnitude, antibody response, and/or combinations thereof are taken. Data gathered from these measurements is then compared with the rate of growth, viremia magnitude, antibody and/or combinations thereof for a known and characterized strain, as a measure of predicted virulence of the new or unknown strain.

Using the methods of the present invention, the rate of PRRS viral growth, viremia magnitude, antibody response, and/or combinations of these characteristics were measured in swine which had one of eight different PRRSV isolate strains administered thereto. Each of these strains had a known level of virulence and clinical disease manifestations. These same characteristics were also measured in swine which had a combination of all eight strains administered thereto.

More specifically, one hundred (100) healthy two-three week old pigs were divided randomly by weight into ten groups with each group having ten pigs. All pigs were tested for PRRS infection using HerdChek® PRRS ELISA 2XR (IDEXX Laboratories Inc., Westbrook, Me.). Eight of the groups received an administration of one of the eight strains, one group received an administration consisting of a combination of all eight strains, and the last group received an administration Eagle's Minimum Essential Medium (EMEM) to act as a control group. A sample of each viral inoculation was retitrated for titer confirmation. Preferably the titer of the administered virus is designed to mimic a natural exposure level of virus. Biological samples in the form of blood were collected at various times throughout the 49-day experiment. Each sample was analyzed by virus isolation, quantitative reverse transcriptase-polymerase chain reaction (RT-PCR), HerdChek® PRRS ELISA 2XR, and PRRSV protein-specific ELISA.

Virus isolation was performed on CL2621 cells by serially diluting serum and combining it with EMEM, gentamicin (Sigma Chemical Co., St. Louis, Mo.) and Fungizone (Invitrogen Corp., Grand Island, N.Y.). The dilutions were then incubated and examined for cytopathic effect (CPE). The Reed-Muench calculation was used to determine titers.

RT-PCR was performed using the QIAamp Viral RNA Mini-Kit® (Qiagen, Inc., Valencia, Calif.) and PRRSV was detected using a single-tube assay by Tetracore, Inc. (Gaithersburg, Md.). To determine virus quantitation, a standard curve was developed and concentrations of the unknown samples were determined by linear extrapolation of the cycle threshold values plotted against the known concentration of the 3' UTR transcript product.

Antibody measurement using ELISA S/P ratios were generated using HerdChek® PRRS ELISA 2XR using the manufacturer's instructions. PRRSV protein-specific ELISA was performed using recombinant isolate VR2332 nucleocapsid (N) and non-structural protein 4 (nsp 4) expressed in BL21 (DE3)-RP cells (Stratagene, La Jolla, Calif.).

All pigs were weighed at the beginning and at the end of the study. Additionally, on every day of the study, each pig was evaluated and scored by a veterinarian for clinical signs of PRRS disease. All resulting data was analyzed statistically and compared on a group-by-group basis.

As used herein, "rate of growth" refers to the measurement of virus replication over time in swine. Preferred examples of this measurement are provided in Example 1. "Viremia magnitudes" as used herein, refers to the concentration of virus circulating in the blood of swine. Preferred examples of this measurement are also provided in Example 1.

DETAILED DESCRIPTION OF THE PREFERRED EMBODIMENTS

Figure 1:
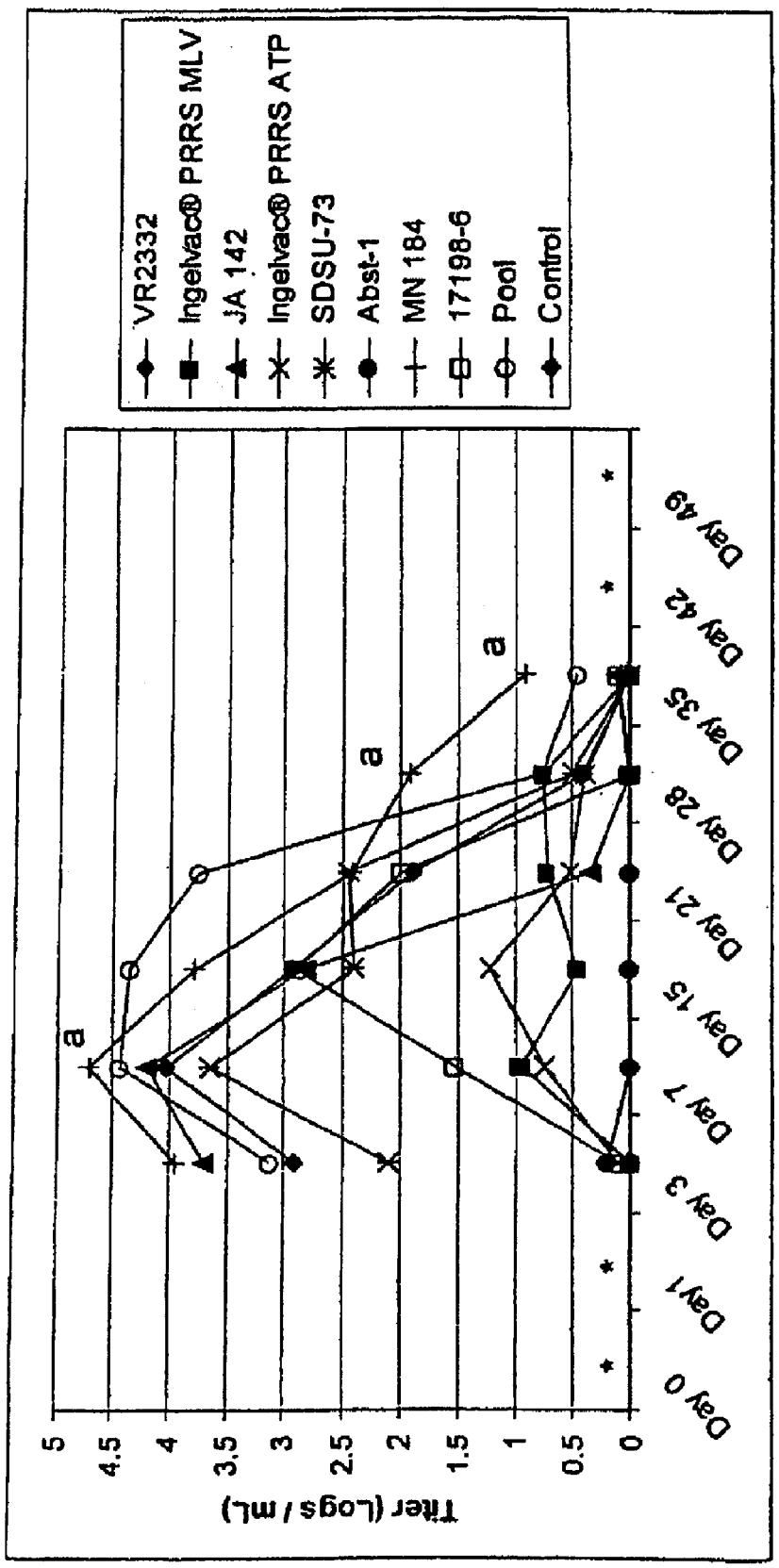
FIG. 1 is a graph of mean serum virus titer versus time expressed as $\log_{10} TCID_{50}$/ml for the swine test of Example 1.

The following examples set forth preferred isolates and procedures in accordance with the present invention. It is to be understood, however, that these examples are provided by way of illustration only, and nothing therein should be deemed a limitation upon the overall scope of the invention.

Example 1

Materials and Methods

One hundred healthy 2-3 week-old pigs were obtained from a PRRS-free commercial herd and were maintained at Veterinary Resources, Inc., Ames, Iowa, under the supervision of a veterinarian. Animals received food and water ad libitum. All of the animal care and laboratory personnel involved with the study were blinded to the treatments given to the various groups of animals. Pigs were tested by Herd-Chek® PRRS ELISA 2XR (IDEXX Laboratories Inc. Westbrook, Me.) to determine if any pigs were infected with PRRSV. All of the pigs for this example tested negative. The pigs were then randomly divided by weight into 10 groups with 10 pigs per group.

A total of eight PRRSV isolates were used in this example. These isolates have been designated VR-2332, Ingelvac® PRRS MLV, JA 142, Ingelvac® PRRS ATP, SDSU 73, Abst-1, MN 184, and 17198-6. These eight isolates span the history of PRRS disease, exhibit a wide range of virulence levels, and represent relevant clinical disease manifestations. All of the virus isolates grew readily on CL2621 cells (CL2621 is a proprietary cell line obtained from NVSL, Ames, Iowa) (an MA-104 monkey kidney cell line). Three of the primary field isolates, VR-2332, JA-142, and SDSU 73, also had attenuated forms, Ingelvac® PRRS MLV (Boehringer Ingelheim Vetmedica Inc., St. Joseph, Mo.), Ingelvac® PRRS ATP (Boehringer Ingelheim Vetmedica Inc., St. Joseph, Mo.), and Abst-1, respectively. These attenuated forms all exhibit low or undetectable virulence that was derived by in vitro passaging to attenuation. The PRRSV isolate ATCC VR-2332 was isolated in 1991 in Minnesota and was used at cell culture passage three. The attenuated form of this virus is commercially available under the trade-name Ingelvac® PRRS MLV. The PRRSV isolate JA 142 (ATTCC No. PAT-6504), provided by William Mengeling, National Animal Disease Center, Ames, Iowa, was isolated in 1997 in Iowa from a severe "abortion-storm" case of reproductive failure and was used at cell culture passage five. The attenuated form of JA 142 is commercially sold under the trade-name Ingelvac®PRRS ATP and has been assigned ATTCC No. VR-2638. PRRSV SDSU 73 (ATCC No. PTA-6322) was recovered in Iowa from a severe case of reproductive disease in 1996 and was used at cell culture passage one. The attenuated form of SDSU 73, designated Abst-1 (ATCC No. PTA-6320), was obtained by 52 passages. The PRRSV isolate 17198-6 (ATCC No. PTA-6321) was obtained from Oklahoma in 1997 from a herd experiencing severe reproductive disease and was used at passage level four. The PRRSV MN 184 isolate (ATCC No. PTA-6319) was obtained in 2001 from a swine farm experiencing severe reproductive disease and sow mortality in southern Minnesota and was provided by Kurt Rossow, University of Minnesota, St. Paul. This isolate was used at a cell culture passage of one. Additionally, a pool consisting of a combination of all isolates was produced.

On day 0, each of the eight PRRSV isolates and the PRRSV pool were diluted to approximately 3.0 $\text{Log}_{10}$ $\text{TCID}_{50}$/ml in Eagle's Minimum Essential Medium (EMEM) (JRH Bioscience, Lenexa, Kans.) containing 4% FBS (JRH Bioscience, Lenexa, Kans.) and administered intranasally to pigs at a dose of 2 ml (1 ml per nostril). The untreated control group received 2 ml of media. The inocula were retitrated on 96-well plates containing three-day-old CL2621 cells for titer confirmation using the Reed-Muench method (Reed et al., 1938). The observed titers administered to pigs, together with a description of the virulence level and isolation information, are shown in Table 1.

TABLE 1

Virulence and Inoculation Titer of Isolates.

| Group | Isolate | Year Isolated | Virulence*** | Titer $\log_{10}\text{TCID}_{50}$/ml |
|---|---|---|---|---|
| 1 | VR 2332 | 1991 | Moderate | 3.43 |
| 2 | Ingelvac ® PRRS MLV* | USDA license 1996 | Attenuated VR2332 | 3.02 |
| 3 | JA 142 | 1997 | High | 3.13 |
| 4 | Ingelvac ® PRRS ATP* | USDA license 1999 | Attenuated JA 142 | 4.14 |
| 5 | SDSU 73 | 1996 | High | 2.75 |
| 6 | Abst-1* | Attenuated 1999 | Attenuated SDSU 73 | 4.18 |
| 7 | MN 184 | 2001 | High | 4.10 |
| 8 | 17198-6 | 1997 | High | 2.81 |
| 9 | Pool** | N/A | High | 3.71 |
| 10 | Control | N/A | N/A | N/A |

*attenuated PRRSV isolates.
**Mixture containing all of the eight isolates
***Summary of lung lesions reported in Symposium on Emerging Diseases, Rome 2003.

The isolates were then compared to determine their genetic similarity through an analysis of their percent sequence identity. Sequence identity was determined by submitting virus samples to the University of Minnesota Diagnostic Laboratory for sequence analysis. The results of ORF 5-6 were provided and then compared to a PRRS virus consensus sequence. Individual base pair differences were noted and then the % sequence identity was compared between isolates. As those of skill in the art are aware, blast searching can also be done at various websites. For example, the University of Minnesota provides a PRRSV database (ccgb.umn.edu/cgi-bin/common/web_blast.cgi) that lists sequences from isolates from 1989-2003. Another frequently used site is the NCBI BLAST link found at ncbi.nlm.nih.gov/BLAST.

As shown by the percent sequence identity and the dendogram in Table 2, the virulent field isolates are quite genetically distinct and represented a diverse group of PRRSV isolates. In contrast, the parental and vaccine PRRSV pairs were nearly genetically identical. The pairwise comparison and dendrogram of Table 2 were generated using the Lasergene software suite of sequence analysis tools (DNASTAR, Inc, (Madison, Wis.)).

TABLE 2

Pairwise comparisons of ORF5 nucleotide sequence of virulent and attenuated PRRSV isolates used in the study.

Percent Identity

| | VR 2332 | Ingelvac PRRS MLV | JA-142 | Ingelvac PRRS ATP | SDSU 73 | Abst-1 | MN 184 | 17198-6 |
|---|---|---|---|---|---|---|---|---|
| VR 2332 | | 99.7 | 91.0 | 90.5 | 90.0 | 89.6 | 86.4 | 90.4 |
| Ingelvac PRRS MLV | 0.3 | | 90.7 | 90.2 | 89.7 | 89.2 | 86.4 | 90.0 |
| JA-142 | 9.7 | 10.1 | | 99.2 | 92.7 | 92.2 | 87.2 | 92.2 |
| Ingelvac PRRS ATP | 10.3 | 10.7 | 0.8 | | 91.9 | 91.4 | 86.4 | 91.4 |
| SDSU 73 | 10.9 | 11.3 | 7.8 | 8.8 | | 99.5 | 87.2 | 91.7 |
| Abst-1 | 11.5 | 11.9 | 8.4 | 9.4 | 0.5 | | 86.7 | 91.2 |
| MN 184 | 15.5 | 15.5 | 14.4 | 15.5 | 14.4 | 15.1 | | 86.1 |
| 17198-6 | 10.5 | 10.9 | 8.8 | 9.7 | 9.0 | 9.6 | 15.9 | |

Percent Divergence

Percent similarity is shown in the upper right and percent divergence is shown in the lower left of the table.
The dendrogram shows the genetic relatedness of the isolates.
The bar indicates 1 nucleotide change per 100 residues.
VR 2332 is the parent isolate of Ingelvac PRRS MLV,
JA-142 is the parent strain of Ingelvac PRRS ATP and
SDSU 73 is the parent strain of Abst-1.

Evaluation of Viremia

Blood samples were collected from each pig in each group by vacutainer on days 0, 1, 3, 7, 15, 21, 28, 35, 42, and 49. Serum was separated from clotted whole blood by centrifugation at 3200×g for 20 minutes. Serum samples were then divided for analysis by virus isolation, $\text{Log}_{10}$ $\text{TCID}_{50}$/ml, quantitative reverse transcriptase-polymerase chain reaction (RT-PCR), HerdChek® PRRS ELISA 2XR, and PRRSV protein-specific ELISA. The serum samples in this study were processed immediately after collection and were chilled on ice within 3 hours of being obtained. The samples were stored for a maximum of 24 hr at 4° C. and at −70° C. thereafter. Serum tested by RT-PCR was frozen at −70° C. the day of collection and stored until the testing could be performed at which time only the number of samples that could be tested within 24 hours were thawed, extracted, and tested.

Virus isolation was performed on three-day-old CL2621 cells for samples collected on days 0, 1, 42, and 49. One hundred µl of serum from each pig on the remaining days of the study was diluted serially by ten-fold dilutions to a final dilution of $10^{-6}$ in tubes containing 900 µl of EMEM, 2% FBS, 50 µg/ml gentamicin (Sigma Chemical Co. St. Louis, Mo.), and 2.5 µg/ml Fungizone (Invitrogen Corporation, Grand Island N.Y.). Four replicates of each dilution were incubated on 96-well plates containing CL2621 cells, at 37° C. and 4.5% $CO_2$ for eight days. Each well then was examined for cytopathic effect (CPE) and the titers were determined using the Reed-Muench calculation.

To obtain viral RNA for quantitative RT-PCR the QIAamp Viral RNA Mini-Kit® (Qiagen Inc. Valencia, Calif.) was used as described in the kit instructions. A commercially available real-time, single-tube, RT-PCR assay for the detection of U.S. PRRSV was provided by Tetracore Inc. (Gaithersburg, Md.) and used to detect PRRSV RNA. A minor groove binding (MOB) 5' nuclease probe and primers were designed by alignment of GenBank isolates and based on conserved areas of the 3' untranslated region (UTR). PRRSV RNA was reverse transcribed in a 25 µl single tube reaction consisting of Tetracore U.S. PRRSV Master Mix (18.9 µl Master mix, 2 µl Enzyme mix 1, 0.1 µl Enzyme mix 2) and 4 µl of extracted RNA. The reaction tubes were loaded into the Smart Cycler II® block (Cepheid, Sunnyvale, Calif.) and software settings of fluorescent detection were set for automatic calculation of the baseline with the background subtraction on. The thermal cycler program consisted of 52° C. for 1800 seconds, 95° C. for 900 seconds, and 45 cycles at 94° C. for 30 seconds, 61° C. for 60 seconds and 72° C. for 60 seconds. A PCR reaction was considered positive if the cycle threshold (Ct) level was obtained at ≦45 cycles. For quantitation, known amounts of serially diluted in vitro transcript RNA product ($1\times10^{-1}$ through $1\times10^8$ copies/µl) were used to generate a standard curve. Copy/ml concentrations of the unknown samples were determined by linear extrapolation of the Ct values plotted against the known concentration of the 3'UTR transcript product.

Antibody Measurement

ELISA S/P ratios were generated by performing the HerdChek® PRRS ELISA 2XR according to the manufacturer's instructions. PRRSV protein-specific ELISA for The HerdChek® was performed with recombinant isolate VR2332 nucleocapsid (N) and nonstructural protein 4 (nsp 4) which were expressed in BL21 (DE3)-RP cells (Stratagene) from the plasmid pET 24b as fusion proteins containing an amino terminal myc-tag and a carboxyl terminal 6× histidine tag. Denatured proteins were dialyzed in 0.1 M Tris HCl, pH 8.0, 6 M guanidine-HCl, 2 mM EDTA and adjusted to a concentration of 3 mg/ml. DTT was added to 300 mM and the solution was filtered through a 0.45 µm membrane. Reduced protein was added into refolding buffer (100 mM Tris HCl, pH 8.0, 0.5 M L-arginine, 8 mM oxidized glutathione, 2 mM EDTA, 10 µM pepstatin A, 10 µM leupeptin, and 1 mM PMSF), filtered (0.22 µm) and stirred overnight. The purified protein was concentrated by tangential flow filtration (Pellicon XL Ultracel PLC 5 kd, Millipore) and dialyzed against 20 mM Tris HCl, pH 8.0. Proteins were analyzed on an Agilent 2100 Bioanalyzer with the Protein LabChip. Purified protein solutions were stored at −80° C.

Protein-specific ELISAs were performed by coating microtiter plates with 100 ng recombinant protein in carbonate buffer, pH 9.6, or with buffer alone. Plates were blocked with 2.5% nonfat dry milk in phosphate-buffered saline containing 0.1% Tween 20 (PBST). One hundred µl of a 1:2000 dilution of serum was applied to duplicate wells for 2 hours, after which plates were washed with PBST and antibody binding was detected by incubation with horseradish peroxidase-conjugated goat-anti swine IgG (heavy+light chains) (KPL, Gaithersburg Md.) diluted 1:5000 for 1 hour, followed by washing and color development with 100 µl of TMB substrate (KPL). Reactions were stopped with 1 M phosphoric acid and plates were read at 450 nm.

Body Weights

All pigs were weighed on day 0 (first day of study) and day 49 (end of study). Pigs were weighed on a portable electronic weigh-bar scale system Weigh-Tronix™ model 615XL, (Weigh-Tronix Inc., Fairmont, Minn.). The scale was calibrated using certified test weights prior to and after each use.

Clinical Scores

On every day of the study each pig was scored by a veterinarian for respiratory signs, behavior, and coughing on a scale of one to four for each clinical sign. A normal animal was given a score of three, maximum clinical illness was a score nine and a dead animal received a score of 12. Samples from all animals that died in the study were submitted to the Iowa State University Veterinary Diagnostic Laboratory for pathological examination.

Statistical Analysis

All data were imported into SAS version 8.02 for data management and analysis. Summary statistics including mean, standard deviation standard error, median and frequency distributions were generated for all out come variables as appropriate. Weight, RT-PCR, and $\text{Log}_{10}$ $\text{TCID}_{50}$/ml data were analyzed by one way ANOVA for overall differences among the treatment groups with pairwise testing for differences between treatment groups by Least Significant Difference t test. All tests for differences between groups were designed as two-sided tests. Differences were considered statistically significant at $p \leq 0.05$.

Some changes were made to the data to facilitate correlation analyses. The $\text{Log}_{10}$ $\text{TCID}_{50}$/ml values listed as <2.00 were set to 1.0. Negative RT-PCR values were set to 1.0 and all RT-PCR values were normalized by transformation to log base 10 before analysis. Control group results were not included in the correlation analyses. Results for each pig were converted to an approximate area under the curve using trapezoidal rule. Area under the curve was computed for the entire study period, from the first observation to day 15, and from day 15 to the last observation, although only the entire study period is shown in the figures.

Results

Virus Isolation and $\text{Log}_{10}$ $\text{TCID}_{50}$/ml Quantification

Before exposure on the day of infection no animals tested positive for PRRSV. At 1 day after intranasal infection, only 13 animals in 5 groups tested positive for virus. However, at 3 days after infection all animals that were infected with field isolates, except for isolate 17198-6, were virus positive with mean $\log_{10} TCID_{50}/ml$ values ranging from 2.1 (SDSU-73) to 3.9 (MN 184). By contrast, animals inoculated with attenuated isolates were uniformly negative by cell culture. These results are provided in FIG. 1. Peak levels of viremia, from 3.6 to 4.6 $\log_{10} TCID_{50}/ml$ were attained on day 7 for four of five virulent isolates and titers remained near or above 2 $\log_{10} TCID_{50}/ml$ in all virulent virus groups for 21 days except for JA 142-infected pigs which had titers below that level.

The levels of viremia in the pigs inoculated with attenuated PRRSV isolates were lower than in pigs inoculated with virulent field isolates. The Abst-1 isolate, with the exception of day 3 post inoculation, was never re-isolated. Ingelvac® PRRS MLV viremia fluctuated between 0.5 and 1.0 $\log_{10} TCID_{50}/ml$ from days 7 to 28, and Ingelvac® PRRS ATP varied between 0.4 and 1.2 $\log_{10} TCID_{50}/ml$ from days 7 to 28. Attenuated isolate viruses were not recovered from serum after day 28, and virus was recovered from only two of the virulent field isolate groups, the pool-infected and MN 184-infected pigs through day 35 (also shown in FIG. 1). Nearly all pigs were nonviremic by virus isolation at days 42 and 49.

Overall, the more virulent isolates were observed to replicate faster and to higher titers in pigs than were the attenuated isolates. Pigs infected with the MN 184 isolate, in particular, showed a very rapid increase in virus replication beginning before day 3 and reaching a peak of over 4.5 $\log_{10} TCID_{50}/ml$ on day 7. After peaking, the MN 184 viremia steadily decreased but still maintained a significantly higher titer (t-test, $p \leq 0.05$) than all other isolates on days 28 and 35. A similar trend was observed in all of the remaining virulent groups, namely VR2332, JA 142, SDSU 73, and the pool (see, FIG. 1). Pigs infected with 17198-6 followed the same general trend described for the MN 184 infected group but not as closely.

Groups of pigs administered the attenuated isolates (Ingelvac® PRRS MLV, Ingelvac® PRRS ATP, and Abst-1) followed a different trend. They showed a moderate increase in viral titer beginning after day 3 that reached a peak between days 7 and 15 at a viral titer more than a log less than any of the virulent exposure groups and several orders of magnitude less than the MN 184-infected group. The titers observed in these attenuated exposure groups then declined to zero on or before day 35 (See FIG. 1).

Virus Quantification by Real Time RT-PCR

Figure 2:
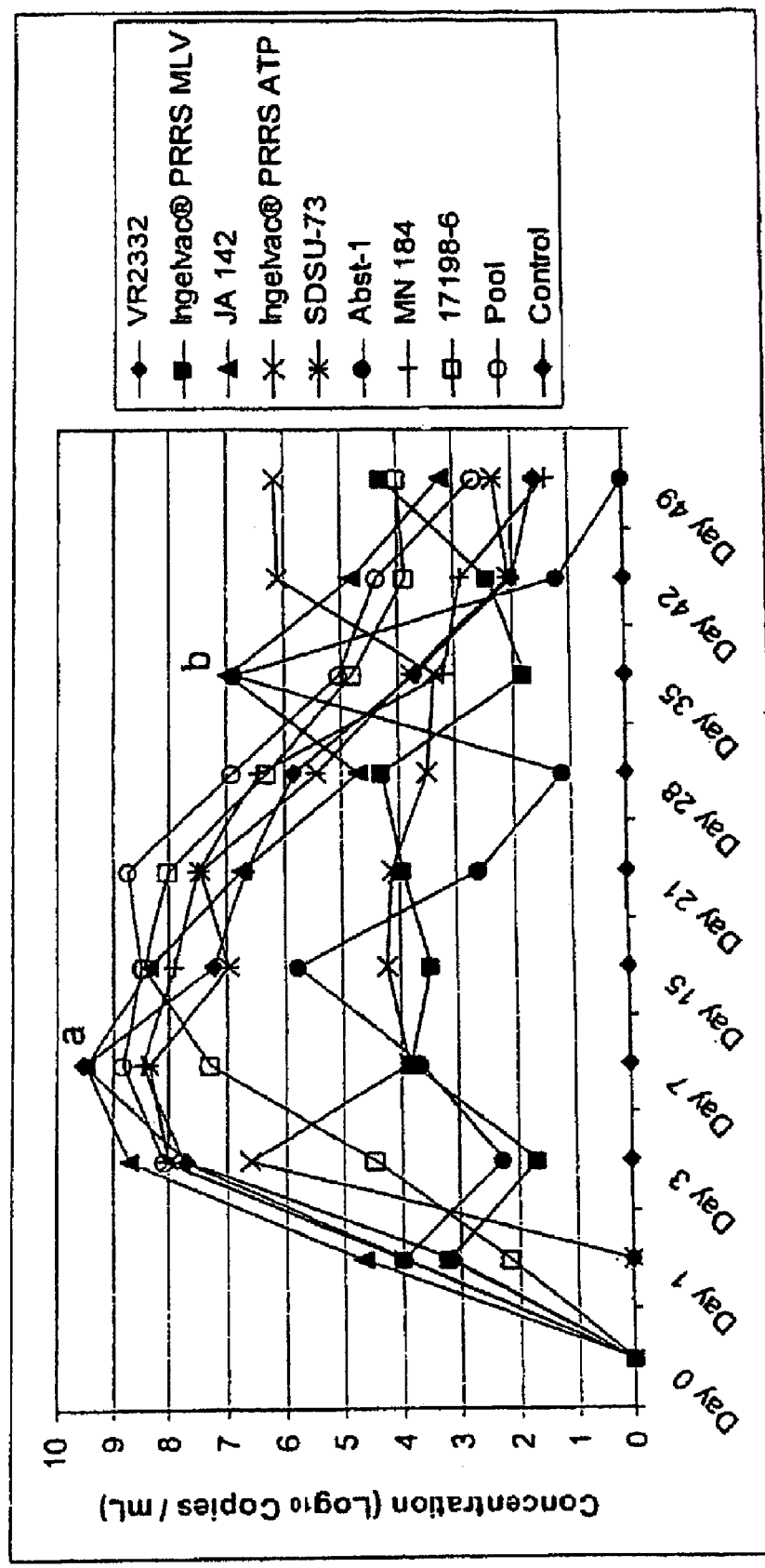
FIG. 2 is a graph of mean PRRSV virus concentration in serum in the swine test of Example 1, as measured by real time RT-PCR.

Levels of viremia were also determined by real time RT-PCR since it was possible that growth on CL2621 cells was not the same for all strains and because RT-PCR might be a more sensitive measure than growth on cells for viremia. As shown in FIG. 2, virulent exposure groups showed a dramatic increase in average concentration on day 1 and all groups peaked above 8 logs/ml between days 7 and 15. The virulent exposure group concentrations then gradually tapered off through the next several weeks, reaching concentrations below 4 logs/ml by day 49.

The attenuated strain exposure groups showed a much less dramatic increase in concentration that also began around day 1 and the average group titer never reached or exceeded 7 logs/ml (FIG. 2). The concentrations observed for the attenuated exposure groups were maintained at fluctuating levels showing a wide range in values in the weeks following the exposure. The fluctuations were primarily due to sporadically high values in a single pig. The three attenuated strain exposure groups all peaked on different days of the study. The Ingelvac® PRRS MLV group peaked at a concentration of 4.31 logs/ml on day 28, the Ingelvac® PRRS ATP group peaked at 6.58 logs/ml on day 3, and the Abst-1 group peaked at 6.85 logs/ml on day 35, which was the highest titer achieved by an attenuated isolate (FIG. 2). Additionally, the average concentration of the virulent isolate groups were observed to be significantly higher ($P<0.05$) than the average concentration of the attenuated strain groups on days 3 and 15, but on day 49 the average concentration of the virulent isolate groups was significantly lower ($P<0.05$) than that of the attenuated isolate groups.

HerdChek® PRRS ELISA 2XR

Figure 3:
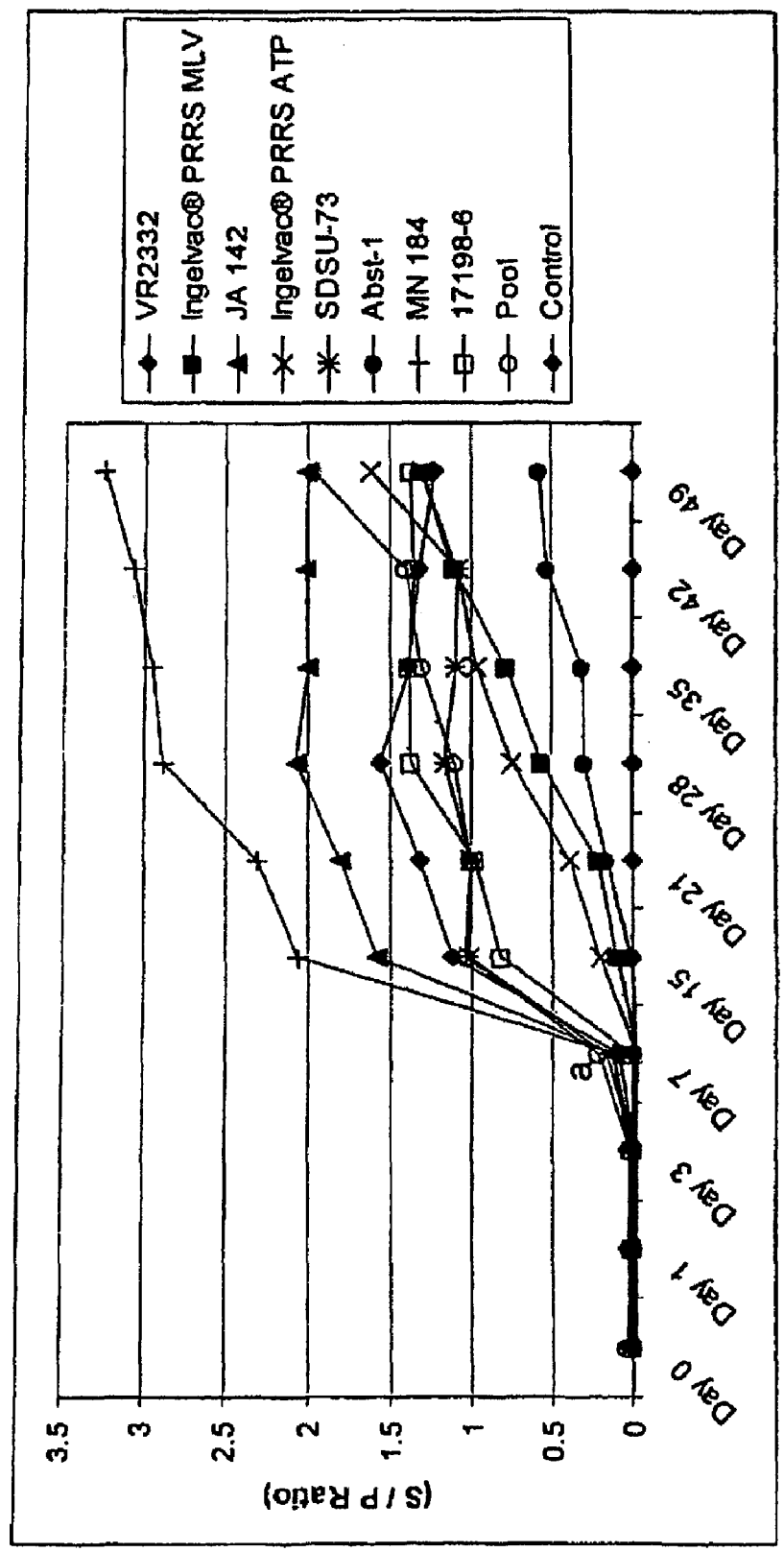
FIG. 3 is a graph of mean S/P ratios versus time using a commercial ELISA assay.

As shown by FIG. 3, the humoral immune response to PRRSV, as measured by HerdChek® PRRS ELISA 2XR S/P ratios, showed that the virulent isolate exposure group averages rose above the 0.4 cutoff for a positive result on day 15. By contrast, the attenuated strain exposure group averages were negative and all three groups remained below 0.4 until after day 21. The Ingelvac® PRRS MLV and Ingelvac® PRRS ATP groups showed positive results on day 28, but the Abst-1 group did not show an average S/P ratio over 0.4 until day 42.

Figure 4:
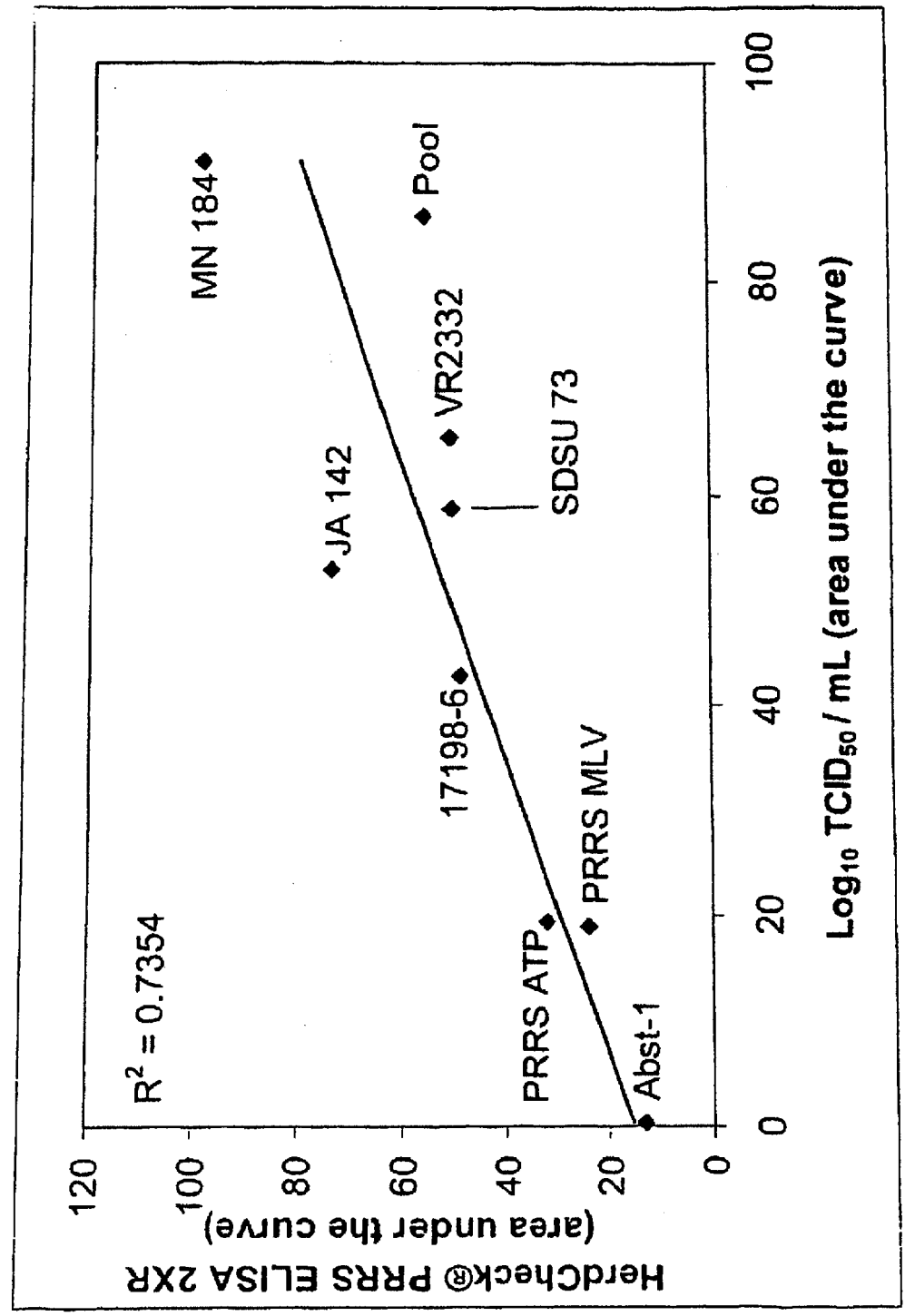
FIG. 4 is a graph illustrating repeated measures analysis for the commercial ELISA assay and the $\log_{10} TCID_{50}$/ml data of Example 1, wherein the group average under the ELISA S/P ratio curve was plotted against the group average area under the $\log_{10} TCID_{50}$/ml.
Figure 5:
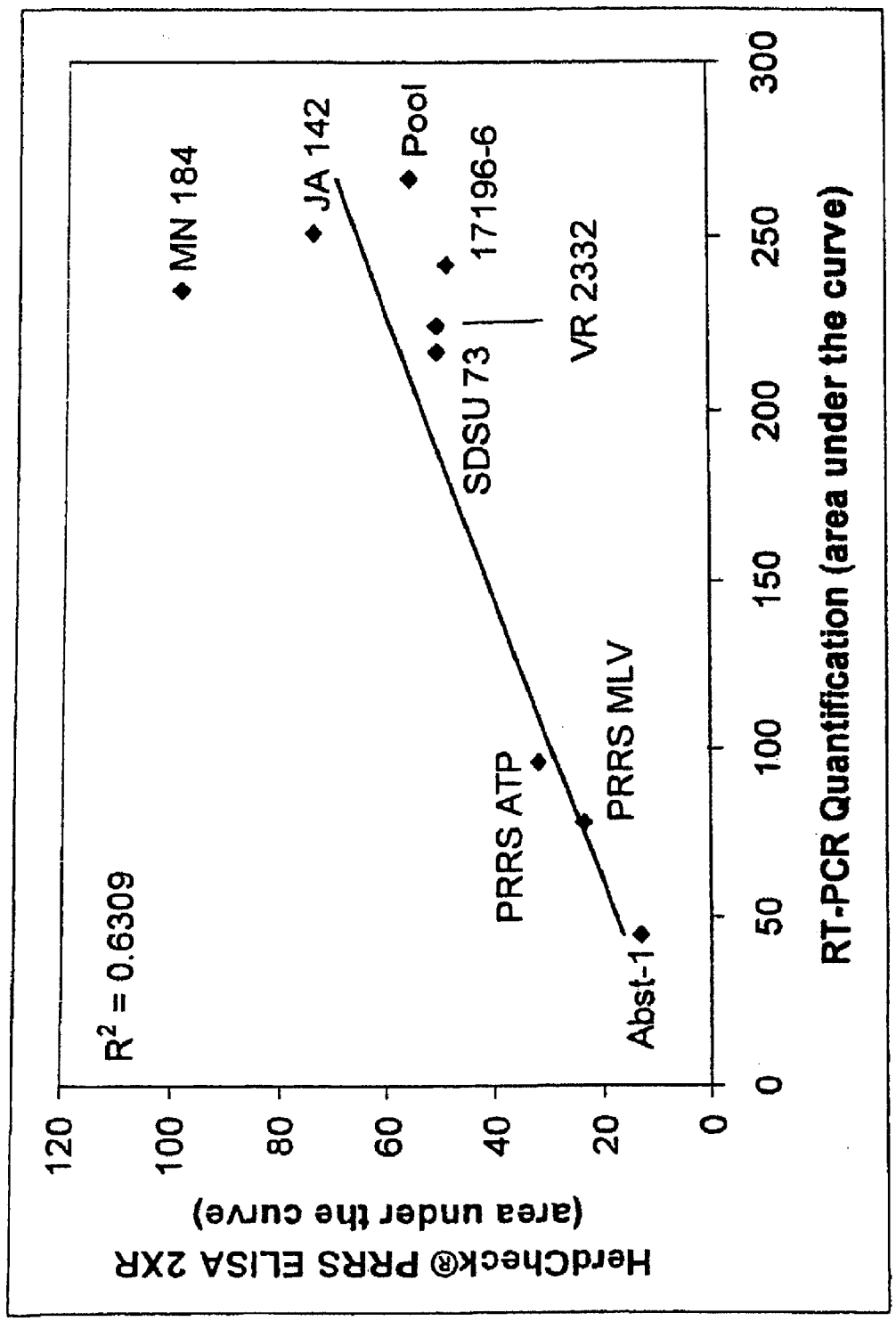
FIG. 5 is a graph illustrating repeated measures analysis for the commercial ELISA assay and RT-PCR concentration data of Example 1, wherein the group average area under the ELISA ratio curve was plotted against the group average area under the RT-PCR concentration curve.

In comparing the humoral response of groups infected with virulent isolates or the pool to groups inoculated with attenuated strains, it was clear that the kinetics and magnitude of the antibody response was associated with the level of viremia, particularly between 14 and 35 days after infection. This observation is further supported by the correlation between viremia levels and humoral antibody responses determined by paired comparisons of HerdChek® PRRS ELISA 2XR S/P ratios to either virus titration or RT-PCR. FIGS. 4 and 5 show that the humoral antibody response is closely associated with viral load over the entire study period with a correlation coefficient $r=0.858$ for virus titration and $r=0.794$ for RT-PCR. These associations were highly significant ($p<0.0001$ in each case). Moreover, attenuated strains show low antibody responses and viral loads, whereas virulent strains show high responses.

PRRSV Protein-Specific ELISA

Figure 6A:
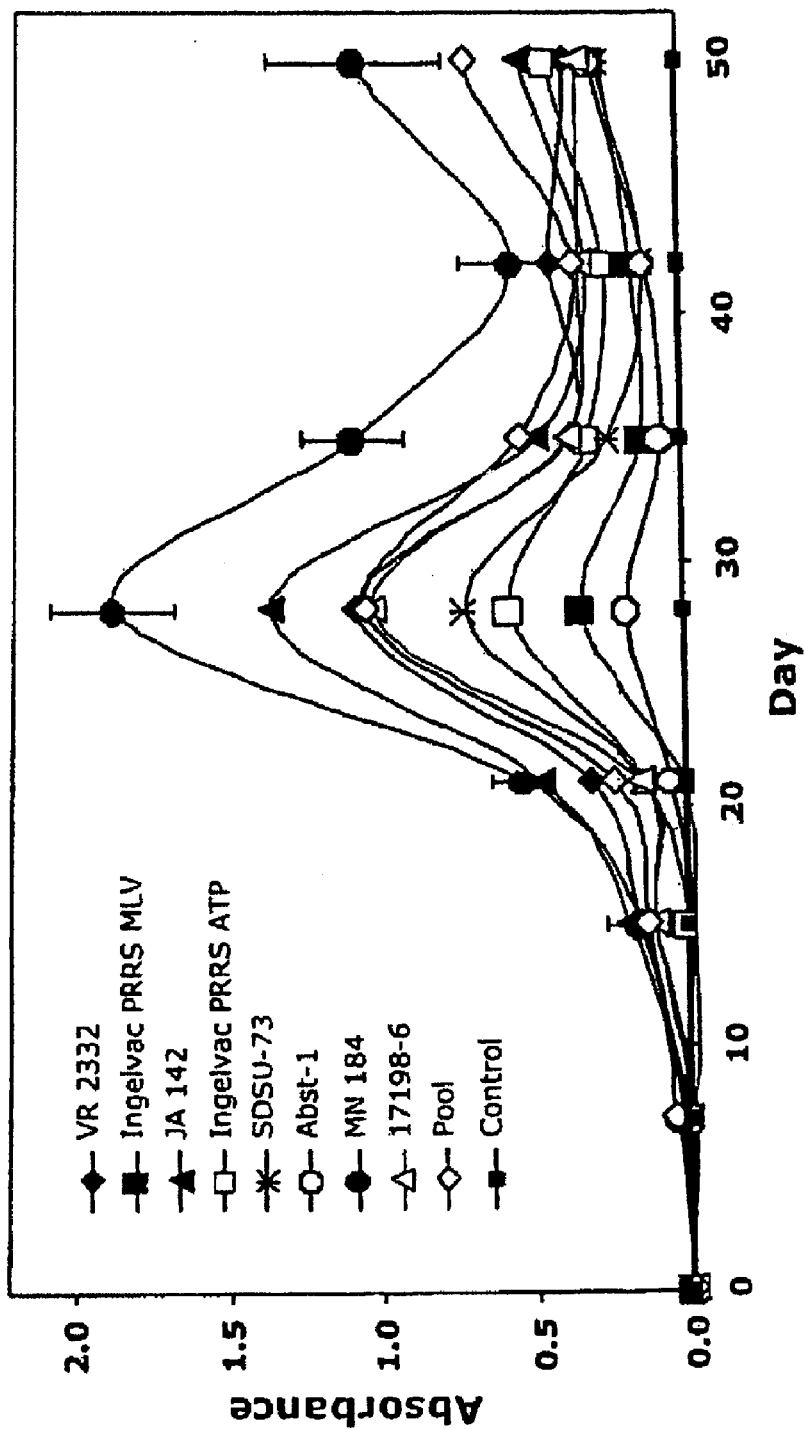
FIG. 6a is a graph of absorbance versus time for Example 1.

To gain additional insight into the relationship between differences in PRRSV inocula and humoral immune responses, the antibody titers against N, the major structural protein, and nsp 4, an essential but minor nonstructural protease, were determined. FIG. 6a illustrates that the kinetics of the nucleocapsid anti-N IgG response were nearly identical in all groups of pigs, with a peak titer on day 28 followed by a sharp decline in the next 7-14 days, after which the levels were maintained or rose slightly between days 42 and 49.

The magnitude of the response for each strain was similar to that found in the HerdChek® PRRS ELISA 2XR results, and consistent with the levels of viremia. The lowest peak titers at day 28 were observed in the groups inoculated with attenuated strains, and the highest titer was attained in pigs infected with the highly virulent MN 184 isolate. By day 49 the anti-N titer was equivalent in all groups except for MN 184 and the pool, suggesting that the humoral response to MN 184 may be qualitatively different. Additionally, only 5 pigs survived to day 49 in each of these two groups, which is reflected in the increased standard error at day 49 in the MN 184 group.

Figure 6B:
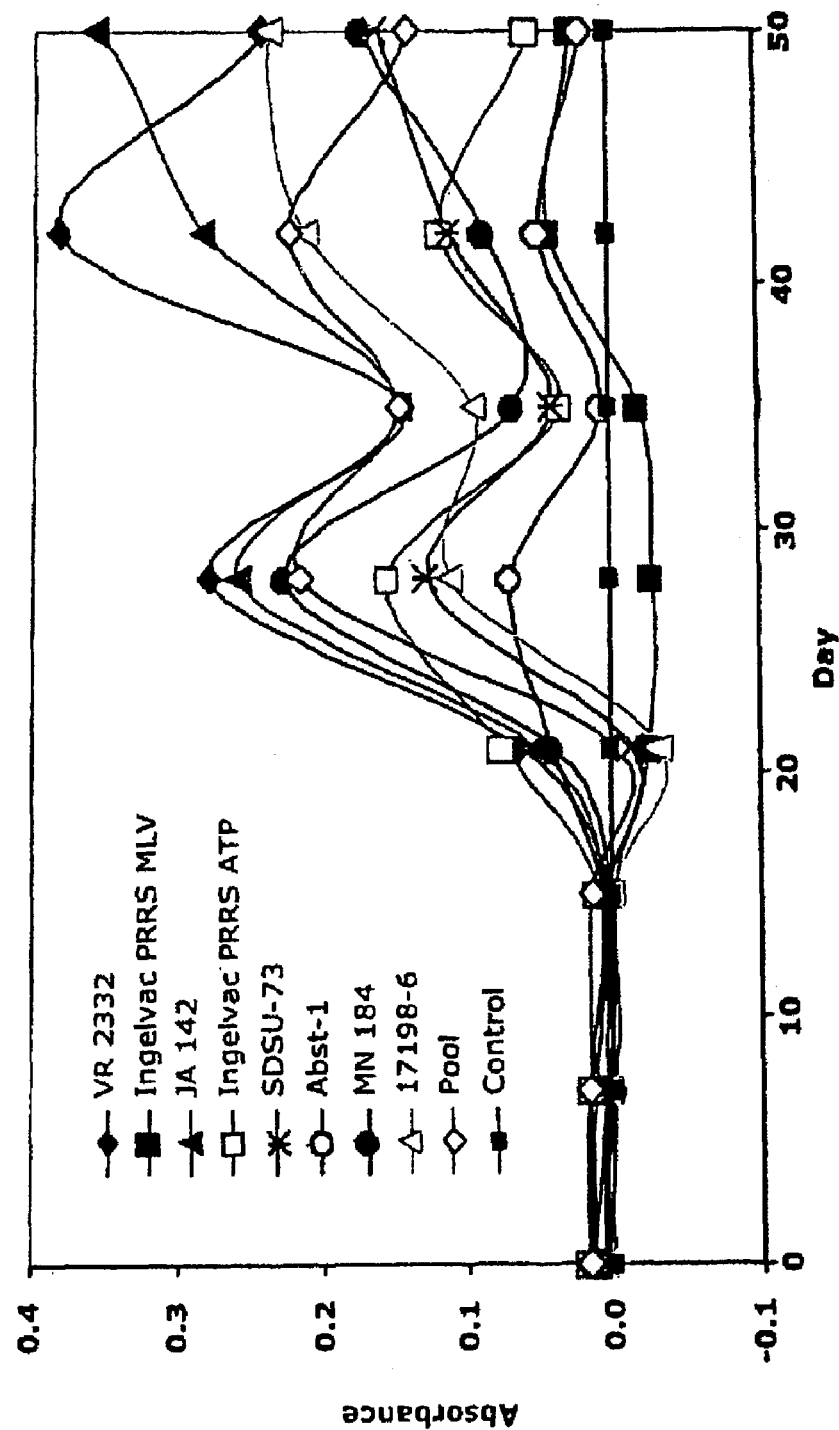
FIG. 6b is a graph of absorbance versus time, illustrating the effect of PRRSV isolate or strain on nsp-4 IgG response, wherein the data are the mean values of 10 animals, except where animals died.
Figure 7:
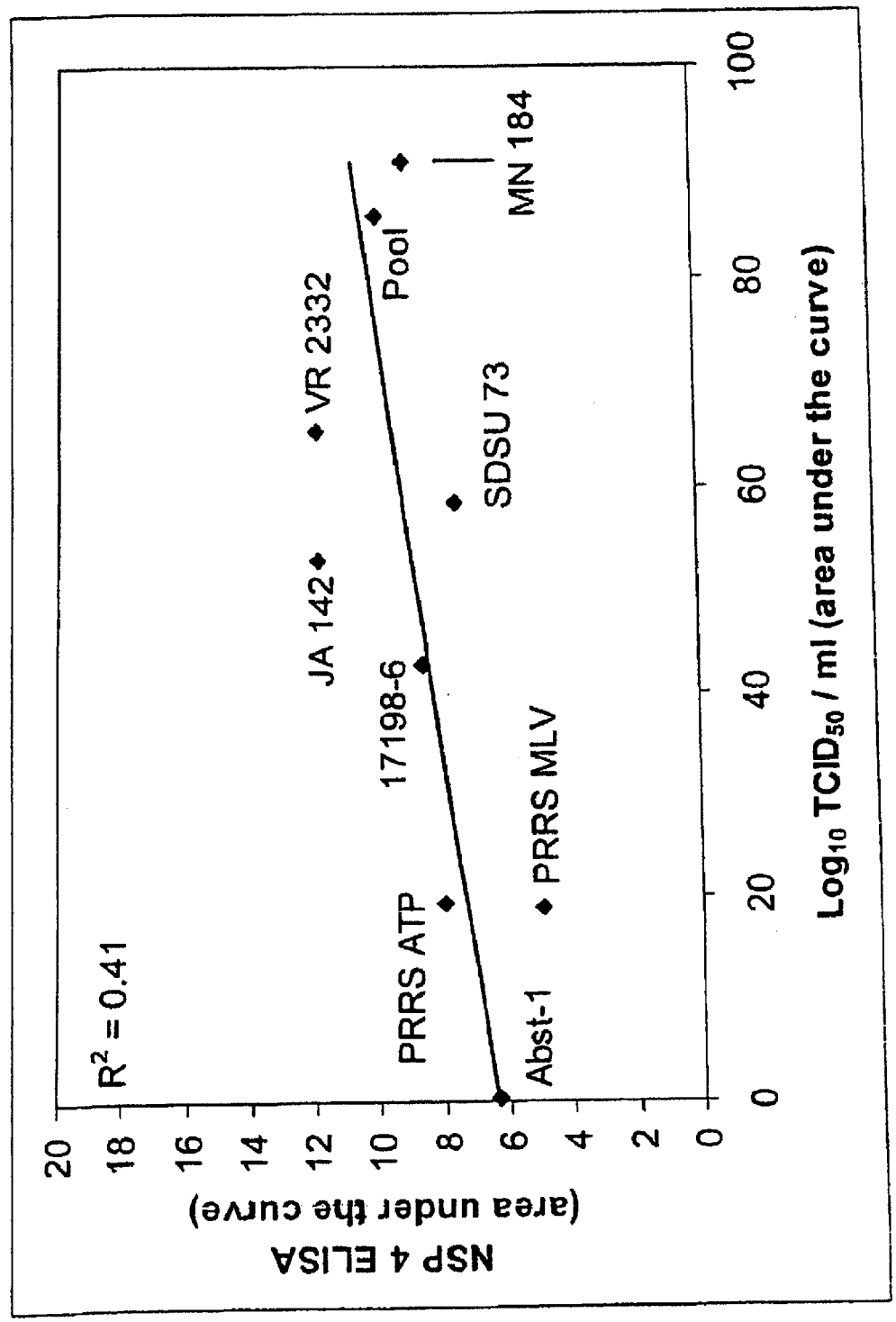
FIG. 7 is a graph illustrating repeated measures analysis using the nsp-4 and $\log_{10} TCID_{50}$/ml data of Example 1, wherein the group average area under the nsp-4 curve was plotted against the group average area under the $\log_{10} TCID_{50}$/ml curve.

As shown by FIG. 6b, the IgG response to nsp 4 was substantially different than to N. No anti-nsp 4 antibody was detected before day 21, the overall response was much weaker, and no significant response was detected in the groups receiving Ingelvac® PRRS MLV and Abst-1. Moreover, the magnitude of the anti-nsp 4 response was not associated with level of viremia. The responses to VR 2332, JA 142, MN 184, and the pool were all equivalent, with a peak at day 28, followed by a decline at day 35, then rising again at day 42, whereas the magnitude, time course and duration of viremia varied among these four groups. FIG. 7 illustrates that when examining the repeated measures analysis, data for the nsp 4 ELISA compared to the $Log_{10}$ $TCID_{50}$/ml data, it can be seen that there is no correlation between level of viremia and nsp 4 humoral antibody response.

Body Weight

There was no significant difference in the mean weight of any of the groups on day 0 of the experiment (P=0.099). On day 49 pigs inoculated with the attenuated strain Abst-1 had the highest mean weight, which was significantly higher then all other groups except for the control group (Table 3). Also, on day 49, the mean weights of all the virulent isolate exposure groups except for the 17198-6 group were significantly lower than the control group (Table 3). The mean weights of the attenuated strain exposure groups Ingelvac® PRRS MLV and Ingelvac® PRRS ATP and the control group were statistically equivalent (Table 3).

TABLE 3

Average Body Weights.

| Isolate | Day 0 | Day 49 |
| --- | --- | --- |
| VR 2332 | 6.38[1] | 33.5[b] |
| Ingelvac ® PRRS MLV | 6.56 | 34.6* |
| JA 142 | 6.42 | 32.7[b] |
| Ingelvac ® PRRS ATP | 6.24 | 35.0* |
| SDSU-73 | 6.59 | 32.9[b] |
| Abst-1 | 6.69 | 39.4[a] |
| MN 184 | 6.73 | 23.7[c] |
| 17198-6 | 6.36 | 34.5* |
| Pool** | 6.51 | 23.0[c] |
| Control | 6.48 | 38.4* |

[1]Weights are in kg. There were no significant differences in mean wt at day 0.
*Indicates statistically equivalent weights among these groups on day 49.
**Pool was a mixture containing all eight isolates.
[a]Significantly greater than all groups except the Control group (p ≦ 0.05).
[b]Significantly less than the Control group.
[c]Significantly less than all other groups.

Clinical Scores

Increases in average clinical scores were observed in only four of the virulent exposure groups: JA 142, SDSU 73, MN 184, and Pool. These higher scores were maintained throughout the study while the remaining groups, both virulent and attenuated exposures, had essentially normal clinical scores for the duration of the study. The only major cause of changes in the average clinical scores observed in this study occurred when one or more animals died in the associated treatment group (Table 4).

TABLE 4

Mortality of Pigs after Exposure

| Group | Strain | Mortality | Day(s) of Death(s) |
| --- | --- | --- | --- |
| 1 | VR 2332 | 0/10 | N/A |
| 2 | Ingelvac ® PRRS MLV | 0/10 | N/A |
| 3 | JA 142 | 1/10 = 10% | 17 |
| 4 | Ingelvac ® PRRS ATP | 0/10 | N/A |
| 5 | SDSU 73 | 2/10 = 20% | 9, 23 |
| 6 | Abst-1 | 0/10 | N/A |
| 7 | MN 184 | 5/10 = 50% | 14, 14, 17, 23, 41 |
| 8 | 17198-6 | 0/10 | N/A |
| 9 | Pool** | 5/10 = 50% | 12, 16, 17, 21, 21 |
| 10 | Controls | 2/10* | 41, 48 |
|  | Attenuated PRRSV | 0/30 = 0% |  |
|  | Virulent PRRSV | 13/60 = 22% |  |

All deaths in treatment groups were attributed to moderate or severe non-suppurative interstitial pneumonia due to PRRSV with secondary bacterial infection.
*Deaths attributed to bacterial pneumonia with no PRRS involvement.
**Pool was a mixture containing all eight isolates.

Figure 8:
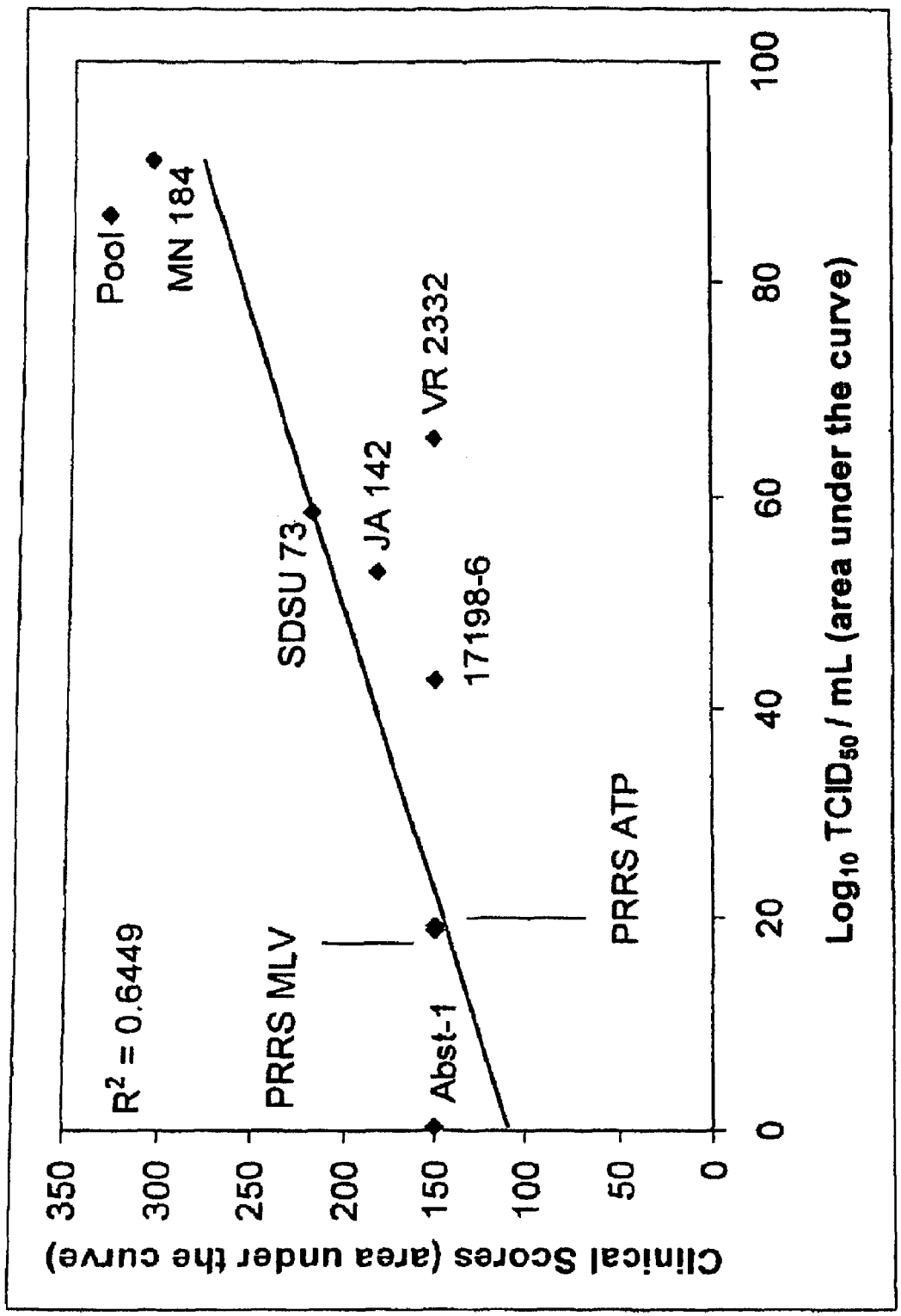
FIG. 8 is a graph of repeated measures analysis using the clinical scores and $\log_{10} TCID_{50}$/ml data of Example 1, wherein the group average under the clinical scores curve was plotted against the group average area under the $\log_{10} TCID_{50}$/ml curve.

The severity of clinical disease was highly associated with viral load (p<0.001 for virus titration). As shown in FIG. 8, the clinical scores were highest for the groups infected with MN 184 and the Pool. Fifty percent of the pigs in each group died, and virus titration indicated that the level of infection was substantially higher than for all other groups. The differences in viral load as determined by RT-PCR were less marked (data not shown) and the correlation of clinical signs with viral load by RT-PCR was less than with virus titration (r=0.556 versus r=0.803, respectively). The clinical scores in group 10 (Control) increased after the death of two pigs from bacterial pneumonia. Both pigs were shown to be PRRSV negative by immunohistochemical staining of lung tissue, negative virus isolation and real-time PCR analyses, and the complete lack of seroconversion by HerdChek® PRRS ELISA 2XR or protein-specific ELISA. Later findings indicated that various bacterial pathogens were present in animals that died unexpectedly during the study these deaths were likely attributed to secondary bacterial infection (Table 5).

TABLE 5

Cause of Mortality after Exposure

| Pig # | Group | Cause of Death | Day of Death |
| --- | --- | --- | --- |
| 993 | JA 142 | PRRS & *Streptococcus suis* | 17 |
| 948 | Neg Control | *Arcanobacterium pyogenes* & *Pasteurella multocida* | 41 |
| 983 | Neg Control | *A. pyogenes* & *P. multocida* | 48 |
| 922 | SDSU 73 | PRRS and bacterial pneumonia* | 9 |
| 918 | SDSU 73 | PRRS and *Escherichia coli* | 23 |
| 973 | MN 184 | PRRS and *Actinobacillus suis* | 14 |
| 992 | MN 184 | PRRS and *A. suis* | 14 |
| 980 | MN 184 | PRRS and *E. coli* | 17 |
| 971 | MN 184 | PRRS and *E. coli* | 23 |
| 958 | MN 184 | PRRS and *E. coli* | 41 |
| 976 | Pool | PRRS and *A. suis* | 12 |
| 970 | Pool | PRRS and V *S. suis* | 16 |
| 972 | Pool | PRRS and *S. suis* | 17 |
| 995 | Pool | PRRS and *S. suis* | 21 |
| 969 | Pool | PRRS and *A. pyogenes* | 21 |

*The diagnostic report indicated "bacterial pneumonia" with no specific agent listed.

DISCUSSION

One objective of this example was to examine various PRRSV isolates with known levels of virulence to determine if there was a relationship with in vivo replication that could be used to predict the virulence of PRRSV isolates without the necessity of performing controlled challenge experiments. Additionally, it was of interest to determine the relationship between isolate virulence, levels of viremia, and the humoral antibody response. Finally, it may be of interest to develop vaccines against the PRRSV isolates that are found to be virulent using the methods of the present invention. It would be a goal to have such vaccines provide some degree of protection against other virulent isolates; however, such cross-effectiveness may not be universal for all PRRSV isolates and further testing would be required. However, it is clear that the present invention provides an effective tool for identifying prime candidates for vaccine development.

In order to test PRRSV isolates under the same conditions it was necessary to use dosages of licensed vaccines that were below the minimum immunizing dose established with the USDA and that were not representative of a commercial dose. Also, the intranasal route of administration of the MLV vaccines used in the study was not in accordance with the USDA label and was only used to mimic a more natural exposure.

The typical commercial dose of the modified live PRRS vaccines (Ingelvac PRRS and Ingelvac PRRS ATP) is much higher than what was used in this experimental trial. These experimentally low doses of modified live PRRS vaccine do not represent the actual product dosage and form used in the field and readily explains the reported serological response. Using a commercial dose of vaccine, serological titers as measured via the IDEXX assay would be detectable by day 14. In this trial using titers of approximately 3 logs, this serological response was delayed and lower. This was to be expected, but was done to insure consistency of titer administration between groups and to facilitate the analysis and comparison between virulent and attenuated isolates. Although not specifically addressed in this Example, the effect of dose is likely much more significant for an attenuated or less virulent virus than it is for a virulent field virus that can quickly grow in and be recovered at over 4 logs/ml in pig serum within 3-7 days of exposure. The higher recommended intramuscular commercial dose gives HerdChek® PRRS ELISA 2XR S/P ratios above the 0.4 cutoff by 14 days post vaccination which is one-half the amount of time observed for the doses used in this study (Roof et al., 2003). The nominal dose used in this study, $2 \times 10^3$ $TCID_{50}$ per animal, caused 50% mortality in groups that received isolate MN 184, and anti-nucleocapsid responses in all groups. Higher doses were not tested since excessive mortality in groups challenged with highly virulent strains would have compromised the study objectives. In addition, previous studies had shown no difference in clinical signs and viremia in young pigs inoculated with PRRSV isolate VR2332 at doses of $10^{2.2}$, $10^{3.2}$ and $10^{4.2}$ $TCID_{50}$ per animal.

Both the $Log_{10}$ $TCID_{50}$/ml and real time RT-PCR results showed that the viremia levels vary significantly among groups following PRRSV exposure. This indicates that the growth rate of PRRSV in pigs is a phenotypic characteristic of the virus independent of possible variation in pig susceptibility to infection. In addition, attenuation of PRRSV by adaptation to growth on CL2621 cells reduced not only its ability to grow in pigs, but altered the kinetics of viral replication so that peak viremia occurred at later times. A similar observation was also made by Chang et al. (2002), who showed that even a limited period of cell culture passage of the moderately virulent PRRSV isolate VR 2332 reduced viral growth in pigs and delayed significantly the time to peak viremia. However, a delayed time to peak viremia is not diagnostic for in vitro cell culture passage or for attenuation, since the highly virulent isolate 17198-6 also showed a delayed time to peak viremia.

Overall, virulent isolates showed substantially higher viremia levels in serum than did attenuated strains at equivalent doses of inoculation. For example, the highest observed virus titer in any of the attenuated isolate exposure groups was 1.22 logs on day 15 in pigs given Ingelvac® PRRS ATP, whereas the lowest titer of any virulent group on day 15 was 2.40 logs in the SDSU 73 group. The peak of viremia at days 3-7 and the levels of virus detected (all >3.5 logs/ml) was highly consistent among virulent PRRSV isolates, though MN 184 was significantly greater in its magnitude and duration, with virus titers still present on days 28 and 35. This supports the concept that highly virulent PRRSV isolates replicate to a substantially higher titer in vivo than do attenuated or lowly virulent isolates, but they do not establish a direct quantitative relationship between level of virulence and level or rate of in vivo growth among wild-type PRRSV (Haynes et al. 1997).

The real time RT-PCR results were statistically very similar to the $Log_{10}$ $TCID_{50}$/ml results, indicating that both methods measure relative levels of infectious virus among groups. The Pearson correlation coefficient between the RT-PCR and $Log_{10}$ $TCID_{50}$/ml day 7 data was 0.89 and for the average real time RT-PCR and $Log_{10}$ $TCID_{50}$/ml results was 0.88. The concentration values determined by real time RT-PCR may have been several orders of magnitude higher than $log_{10}$ $TCID_{50}$/ml values for several reasons, including differences between the frequency of viral particles containing the target amplicon and particles that are fully infectious on CL2621 cells, and the presence of neutralizing antibodies that could lower infectivity (Dianzani et al., 2002). However, neutralizing antibody is unlikely to account for the difference, because it was observed at all time points, including times before which an anti-PRRSV antibody response had been produced.

The copies/ml values determined by real-time PCR were higher than the infectious titer values measured in cell culture by $TCID_{50}$/ml. This is because a standard curve based on the copies of genome of the virus is routinely used for quantitative PCR which directly amplifies a genomic sequence of the virus rather than known infectious virions. Biologic assays such as cell culture do measure the presence of infectivity, however, they may not count all of the infectious particles present in a preparation. Factors that could affect the infectious titer such as cell culture conditions and in vivo antibodies, which may neutralize virus, have been observed in other studies, underestimating the amount of infectious virus measured in $TCID_{50}$/ml in sera. Alternatively, some non-infectious or replication-defective virus may be present which would be reflected by higher copy numbers.

In general, the ELISA observations support the concept that the magnitude of the humoral immune response is related to the level of viral replication during acute infection. The trend indicated in FIGS. 4 and 5 illustrates this relationship. A slower and less intense humoral immune response was triggered by the cell-culture attenuated virus isolates, whereas a faster and more intense humoral immune response was triggered by the virulent isolates. In addition these observations also demonstrate that at least two factors, isolate type and infectious dose, impact relative S/P ratio values in the HerdChek® PRRS ELISA 2XR. Although the ELISA results shown in FIG. 3 indicate a clear positive or negative average group response, it is important to note the variability among individual animals. Some pigs within attenuated virus groups were positive before day 21, and some pigs in the virulent groups remained negative up to day 21.

Analysis of specific antibody responses to N and nsp 4 show that immune responses to PRRSV vary in intensity independently of the inoculating isolate. Antibody responses to the N protein in animals that were inoculated with the highly virulent isolates MN 184 and JA 142 showed a trend similar to that of all the isolates but to a higher magnitude. Pigs inoculated with MN 184 and JA 142 also had the highest viral titers, as shown in FIGS. 1 and 2. This indicates that the level of humoral immune response may be related to the viral load in acute infection as measured by viral titer. Interestingly, the time course of response was the same in all groups, even though the time to peak titer was delayed for highly virulent strain 17198-6 and the attenuated strains. The nsp 4 antibody response, by contrast, was low at all of the time points and for all of the isolates, both attenuated and virulent. The time course of anti-nsp 4 response was equivalent in all of the groups despite differences in the time to peak viral load among groups, as observed for the anti-N antibody response. All pigs had low anti-nsp 4 responses as shown in FIG. 7.

These observations indicate that some of the PRRSV proteins elicit a more robust response from the host immune system regardless of exposure isolate virulence. However, the observations also indicate that the magnitude of the immune response to the more immunogenic proteins is likely related to the virulence of the exposure isolate, or the ability of the isolate to replicate in vivo. It also is possible that differences in antibody response might be due simply to genetic differences among isolates that result in differences in antigenic reactivity such that antibodies directed against N and nsp 4 of other isolates do not react or react poorly to the recombinant proteins expressed from isolate VR2332 that were used to coat the ELISA plates. However, several lines of evidence suggest that the observed differences in antibody levels reflect immunologically relevant responses. Isolate MN 184 shows the greatest genetic difference from VR2332, as determined by ORF 5 comparisons, yet has the highest anti-N antibody response. Kapur et al. (1996) showed previously that relative differences among PRRSV isolates in one open reading frame are also present in other open reading frames. Additionally, individual proteins contain conserved and non-conserved regions (e.g. Kapur et al., 1996) and extensive immunogenic reactivity may be directed toward the conserved epitopes (Ostrowski et al., 2002). Nevertheless, ELISA results based on antibody reactions with purified PRRSV proteins may be affected by genetic and antigenic variation, and these effects must be considered. Refolding of recombinant proteins was performed, but no differences were observed between ELISA plates coated with nonrefolded or refolded proteins.

It was noted that at approximately 4 to 5 weeks after inoculation, a relatively large decrease in the antibody response to both the N and nsp 4 proteins occurred. A similar peak of 1 to 2 weeks followed by a decline of antibody reactivity was previously noted by Foss et al. (2002) for GP5, the major envelope glycoprotein. Taken together, these observations suggest that the response to individual viral proteins likely does not represent the full picture of the pig's immune response to PRRSV since the humoral immune response as measured by the HerdChek® PRRS ELISA 2XR does not show a similar transient peak of antibody reactivity.

Reduced growth and mortality were the key correlates of virulence and viral in vivo growth rate. The lower mean weight observed in the virulent isolate exposure groups most likely reflected a difference in the ability of a PRRSV isolate to replicate in viva and induce a more severe illness in the pig. These observations are consistent with previously reported data that PRRSV infection may cause anorexia with a 25 to 40 percent reduction in daily weight gain (Thacker, 2003). The clinical scores of animals exposed to the virulent isolates showed rapid increases shortly after the inoculation, whereas there was virtually no change in the scores of the attenuated virus exposure animals. This increase in clinical signs was reflected in the observed death rates of 50%, 20%, and 10% in the virulent exposure groups receiving PRRS isolates MN 184, SDSU 73, and JA 142, respectively. In contrast, the attenuated exposure groups incurred no deaths. The relationship between rapid viral growth and viral pathogenesis under the same conditions of viral exposure were most evident in comparing the groups exposed to MN 184 and Abst-1. The inoculation titers were virtually the same, 4.10 logs/ml and 4.18 logs/ml, respectively, and yet, as indicated in FIG. 8, there were remarkable differences in the way the two isolates affected pigs. The Abst-1 isolate was nearly inert, it hardly replicated in vivo and caused no clinical signs. By contrast, the MN 184 isolate replicated to extremely high titers in vivo and caused severe clinical signs, resulting in the death of 50% of exposed animals. Also notable, the group of pigs exposed to the pool of all virus isolates showed about the same virological, clinical, and immunological responses as pigs exposed to MN 184. This finding indicates that the most rapidly replicating virus in a mixed infection is likely to outcompete other isolates so that the net result is essentially the same as an infection with the single isolate having the highest growth potential.

The notable in vivo differences between virulent and attenuated PRRSV isolates shed light on the relationship between the virulence of an isolate and its in vivo growth and replication. When administered at equivalent doses in pigs, the more virulent isolates show $Log_{10}$ $TCID_{50}$/ml titers and RT-PCR concentrations that are exponentially higher than the attenuated isolates. The virulent isolates induce a more rapid and intense humoral immune response. The virulent isolates negatively affect weight gain and induce higher death rates and more severe clinical signs as compared to the attenuated isolates.

In conclusion, the example and tests in the present application indicate that attenuated and virulent PRRSV isolates induce remarkably different clinical signs, as well as immune responses that differ in intensity. These differences are attributed to the ability of the virus to replicate in vivo, a phenotypic characteristic that can be measured quantitatively in serum samples and may be developed for predicting the virulence of PRRSV isolates.

REFERENCES

The teachings and content of each of the following references are incorporated by reference herein.

Albina, E., Piriou, L., Hutet, E., Cariolet, R., L'Hospitalier, R., 1998. Immune Responses in Pigs Infected with Porcine Reproductive and Respiratory Syndrome Virus (PRRSV). *Vet. Immunol. Immunopathol.* 61, 49-66.

Andreyev, V. G., Wesley, R. D., Mengeling, W. L., Vorwald, A. C., Lager, K. M., 1997. Genetic Variation and Phylogenetic Relationships of 22 Porcine Reproductive and Respiratory Syndrome Virus (PRRSV) Field Strains Based on Sequence Analysis of Open Reading Frame 5. *Arch. Virol.* 142, 993-1001.

Cavanagh, D., 1997. Nidovirales: a New Order Comprising Coronaviridae and Arteriviridae. *Arch. Virol.* 142, 629-633.

Chang, C. C., Yoon, K. J., Zimmerman, J. J., Harmon, K. M., Dixon, P. M., Dvorak C. M. T., Murtaugh, M. P., 2002. Evolution of Porcine Reproductive and Respiratory Syndrome Virus During Sequential Passages in Pigs. *J. Virology.* 76, 4750-4763.

Grebennikova, T. V., Clouser, D. F., Vorwald, A. C., Musienko, M. I., Mengeling, W. L., Lager, K. M., Wesley, R. D., Biketov, S. F., Zaberezhny, A. D., Aliper, T. I., Nepoklonov, E. A., 2004. Genomic Characterization of Virulent, Attenuated, and Revertant Passages of North American Porcine Reproductive and Respiratory Syndrome Virus Strain. *Virology.* 321, 383-390.

Dianzani F., G. Anelli, E. Riva, O. Turriziani, L. Antonelli, S. Tyring, D. Carrasco, H. Lee, D. Nguyen, J. Pan, J. Poast, M. Cloyd, S. Baron. 2002. Is Human Immunodeficiency Virus Rna Load Composed Of Neutralized Immune Complexes? *Journal of Infectious Diseases.* 185:1051-1054.

Foss, D. L., Zilliox, M. J., Meier, W., Zuckermann, F., Murtaugh, M. P. 2002. Danger Signals Increase the Immune Response to Porcine Reproductive and Respiratory Syndrome Virus. *Virus Res.* 15, 557-566.

Halbur, P. G., Pallares, F. J., Rathje, J. A., Evans, R., Hagemoser, W. A., Paul, P. S., Meng, X. J., 2002. Effects of Different Us Isolates of Porcine Reproductive and Respiratory Syndrome Virus (PRRSV) on Blood and Bone Marrow Parameters of Experimentally Infected Pigs. *Vet Rec.* 21, 344-348.

Halbur, P. G., Paul, P. S., Meng, X. J., Lum, M. A., Andrews, J. J., Rathje, J. A., 1996. Comparative Pathogenicity of Nine Us Porcine Reproductive and Respiratory Syndrome Virus (PRRSV) Isolates in a Five-week-old Cesarean-derived, Colostrums-deprived Pig Model. *J. Vet. Diagn. Invest.* 8, 11-20.

Haynes, J. S., Halbur, P. G., Sirinarumitr, T., Paul, P. S., Meng, X. J., Huffman, E. L., 1997. Temporal and Morphologic Characterization of the Distribution of Porcine Reproductive and Respiratory Syndrome Virus (PRRSV) by in Situ Hybridization in Pigs Infected with Isolates of PRRSV That Differ in Virulence. *Vet. Pathol.* 34, 39-43.

Hill, H., 1990. Overview And History Of Mystery Swine Disease (Swine Infertility And Respiratory Syndrome). In *Mystery Swine Disease Communication Meeting Denver, Colo., pp.* 29-31.

Kapur, V., Elam, M. R., Pawlovich, T. M. Murtaugh, M. P. 1996. Genetic Variation In PRRS Virus Isolates In The Midwestern United States. *J. Gen. Viral.* 77, 1271-1276.

Key, K. F., Haqshenas, G., Guenette, D. K., Swenson, S. L., Toth, T. E., Meng, X. J., 2001. Genetic Variation And Phylogenetic Analyses Of The Orf5 Gene Of Acute Porcine Reproductive And Respiratory Syndrome Virus Isolates. *Vet. Micro.* 83, 249-263.

Labarque, G., Van Gucht, S., Van Reeth, K., Nauwynck, H., Pensaert, M., 2003. Respiratory Tract Protection Upon Challenge Of Pigs Vaccinated With Attenuated Porcine Reproductive And Respiratory Syndrome Virus Vaccines. *Vet. Micro.* 95, 187-197.

Meng, X. J., 2000. Heterogeneity of Porcine Reproductive and Respiratory Syndrome Virus: Implications for Current Vaccine Efficacy and Future Vaccine Development. *Vet. Micro.* 74, 309-329.

Mengeling, W. L., Lager, K. M., Vorwald, A. C., Clouser, D. F., 2003a. Comparative Safety and Efficacy of Attenuated Single-strain and Multi-strain Vaccines for Porcine Reproductive and Respiratory Syndrome. *Vet. Micro.* 93, 25-38.

Mengeling, W. L., Lager, K. M., Vorwald, A. C., Koehler, K. J., 2003b. Strain Specificity of the Immune Response of Pigs Following Vaccination with Various Strains of Porcine Reproductive and Respiratory Syndrome Virus. *Vet. Micro.* 93, 13-24

Mengeling, W. L., Lager, K. M., Vorwald, A. C., 1998. Clinical Effects of Porcine Reproductive and Respiratory Syndrome Virus on Pigs During the Early Postnatal Interval. *Amer. J. Vet Res.* 59, 52-55.

Murtaugh, M. P., K. S. Faaberg, J. Laber, M. Elam, and V. Kapur. 1998. Genetic Variation In The PRRS Virus. *Adv. Exp. Med. Biol.* 440, 787-794.

Murtaugh, M. P., Xiao, Z., Zuckermann, F., 2002. Immunological Responses Of Swine To Porcine Reproductive And Respiratory Syndrome Virus Infection. *Viral Immunology.* 15, 533-547.

Nodelijk, G., de Jong, M. C. M., van Leengoed, L. A. M. G., Wensvoort, G., Pol, J. M. A., Steverink, P. J. G. M., Verheijden, J. H. M., 2001. A Quantitative Assessment Of The Effectiveness Of PRRSV Vaccination In Pigs Under Experimental Conditions. *Vaccine* 19, 3636-3644.

Ostrowski, M, Galeota, J. A., Jar, A. M., Platt, K. B., Osorio, F. A., Lopez, O. J. 2002. Identification Of Neutralizing And Nonneutralizing Epitopes In The Porcine Reproductive And Respiratory Syndrome Virus Gp5 Ectodomain. *J. Viral.* 76, 4241-4250.

Opriessnig, T., Halbur, P. G., Yoon, K. J., Pogranichniy, R. M., Harmon, K. M., Evans, R., Key, K. F., Pallares, F. J., Thomas, P., Meng, X. J., 2002. Comparison Of Molecular And Biological Characteristics Of A Modified Live Porcine Reproductive And Respiratory Syndrome Virus (PRRSV) Vaccine (Ingelvac PRRS Mlv), The Parent Strain Of The Vaccine (Atcc Vr2332), Atcc Vr2385, And Two Recent Field Isolates Of PRRSV. *J. Viral.* 76, 11837-11844.

Pejsak, Z., Stadejek, T., Markowska-Daniel, I., 1997. Clinical Signs And Economic Losses Caused By Porcine Reproductive And Respiratory Syndrome Virus In A Large Breeding Farm. *Vet. Micro.* 55, 317-322.

Reed, L., Muench, H., 1938. A Simple Method For Estimating Fifty Percent Endpoints. *Am J Hyg.* 27, 493-497.

Roof, M. B., Vaughn, E. M., Burkhart, K. M., Faaberg, K. S. 2003. Efficacy Of Modified Live Virus Porcine Reproductive And Respiratory Syndrome Virus Vaccines Against Heterologous Respiratory Challenge. *Proc. $4^{th}$ Inter. Symp. Emerging Re-emerging Pig Diseases.* pp. 117-118.

Thacker, B., 2003. Clinical Manifestations Of PRRS Virus. In: *Zimmerman, J., Yoon, K J. (Eds.), 2003 PRRS Compendium Second Edition. National Pork Board, Des Moines Iowa USA,* pp. 7-12.

Thanawongnuwech, R., Halbur, P. G., Ackermann, M. R., Thacker, E. L., Royer, R. L., 1998. Effects Of Low (Modified-live Virus Vaccine) And High (Vr-2385)-virulence Strains Of Porcine Reproductive And Respiratory Syndrome Virus On Pulmonary Clearance Of Copper Particles In Pigs. *Vet. Pathol.* 35, 398-406.

Yuan, S., Mickelson, D., Murtaugh, M. P., Faaberg, K. S., 2001. Erratum To "Complete Genome Comparison Of Porcine Reproductive And Respiratory Syndrome Virus Parental And Attenuated Strains". *Virus Research.* 79, 189-200.

We claim:

1. A Porcine reproductive and respiratory syndrome (PRRS) virus isolate SDSU 73 deposited under ATCC No. PTA-6322.

2. An immunogenic composition comprising an attenuated porcine reproductive and respiratory syndrome (PRRS) virus isolate and a pharmacologically compatible carrier, wherein said attenuated PRRS is an attenuated SDSU 73 virus isolate deposited under ATCC No. PTA-6322.

3. The immunogenic composition of claim 2 which is a modified live vaccine.

4. A method of vaccinating a swine against PRRS comprising administering to said swine an immunogenic composition of claim 2.

* * * * *